US009533124B2

(12) United States Patent
Mack et al.

(10) Patent No.: US 9,533,124 B2
(45) Date of Patent: Jan. 3, 2017

(54) REPERFUSION INJURY DEVICES

(75) Inventors: Matthew M. Mack, Chicago, IL (US); Jeffrey Allen Spaeder, Evanston, IL (US); Kevin Joe Ehrenreich, San Francisco, CA (US); John L. Toner, Libertyville, IL (US); Paul Macke Consigny, San Jose, CA (US); Syed Faiyaz Ahmed Hossainy, Hayward, CA (US); Shubhayu Basu, Solon, OH (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1186 days.

(21) Appl. No.: 13/086,664

(22) Filed: Apr. 14, 2011

(65) Prior Publication Data

US 2012/0265283 A1 Oct. 18, 2012

(51) Int. Cl.
*A61M 25/10* (2013.01)
*A61F 2/958* (2013.01)
*A61M 25/00* (2006.01)

(52) U.S. Cl.
CPC ........ *A61M 25/1011* (2013.01); *A61M 25/104* (2013.01); *A61M 25/1018* (2013.01); *A61M 25/10185* (2013.11); *A61F 2/958* (2013.01); *A61M 2025/0004* (2013.01); *A61M 2025/0006* (2013.01); *A61M 2025/1013* (2013.01); *A61M 2025/1015* (2013.01); *A61M 2025/1052* (2013.01); *A61M 2025/1079* (2013.01)

(58) Field of Classification Search
CPC . A61F 2/958; A61F 2/013; A61M 2025/0078; A61M 2025/1097; A61M 2025/1095; A61M 1/3613

USPC .......................................................... 623/1.11
See application file for complete search history.

(56) References Cited

U.S. PATENT DOCUMENTS

| 4,861,520 | A | 8/1989 | Van't Hooft et al. |
| 5,011,468 | A | 4/1991 | Lundquist et al. |
| 5,336,184 | A | 8/1994 | Teirstein |
(Continued)

FOREIGN PATENT DOCUMENTS

WO    WO 01/41861 A1    6/2001

OTHER PUBLICATIONS

ISR/WO for PCT/US2010/033276 dated Jul. 30, 2010.
(Continued)

*Primary Examiner* — Diane Yabut
(74) *Attorney, Agent, or Firm* — Randy Shen; Blakely, Sokoloff, Taylor & Zafman LLP

(57) ABSTRACT

A catheter configured for performing reperfusion by alternatively occluding a vessel so as to prevent fluid flow and removing that occlusion to allow fluid flow is described. A first catheter includes an outer member and a retractable valve to allow and prevent fluid flow in the vessel. A second catheter includes a sheathed expansion member that can be deployed and recaptured to prevent and allow, respectively, fluid flow. A third catheter includes an angioplasty balloon to open a vessel occlusion, in which an occlusion balloon is used to allow and disallow fluid flow. A fourth catheter includes an expandable member for providing mechanical plunging action to urge thrombotic material to a more distal location. A fifth catheter includes an accessory catheter that can be used to perform reperfusion with another catheter. A sixth catheter includes an inner balloon within an outer balloon configured to perform reperfusion.

7 Claims, 31 Drawing Sheets

(56) References Cited

U.S. PATENT DOCUMENTS

| | | | |
|---|---|---|---|
| 5,425,713 | A | 6/1995 | Taylor et al. |
| 5,500,013 | A | 3/1996 | Buscemi et al. |
| 5,925,054 | A | 7/1999 | Taylor et al. |
| 5,972,019 | A | 10/1999 | Engelson et al. |
| 5,976,119 | A | 11/1999 | Spears et al. |
| 6,071,305 | A | 6/2000 | Brown et al. |
| 6,280,457 | B1 | 8/2001 | Wallace et al. |
| 6,295,990 | B1 | 10/2001 | Lewis et al. |
| 6,435,189 | B1 * | 8/2002 | Lewis et al. ............... 128/898 |
| 6,436,087 | B1 | 8/2002 | Lewis et al. |
| 6,746,465 | B2 | 6/2004 | Diederich et al. |
| 6,767,345 | B2 | 7/2004 | St. Germain et al. |
| 6,900,008 | B2 | 5/2005 | Vinten-Johansen et al. |
| 6,986,880 | B2 | 1/2006 | Coniglione et al. |
| 7,166,097 | B2 | 1/2007 | Barbut |
| 7,220,252 | B2 | 5/2007 | Shah |
| 7,335,192 | B2 | 2/2008 | Keren et al. |
| 7,364,566 | B2 | 4/2008 | Elkins et al. |
| 7,468,027 | B2 | 12/2008 | Barbut et al. |
| 7,468,070 | B2 | 12/2008 | Henry et al. |
| 7,686,781 | B2 | 3/2010 | Vinten-Johansen |
| 2001/0010013 | A1 * | 7/2001 | Cox .................. A61F 2/91 623/1.15 |
| 2003/0078538 | A1 | 4/2003 | Neale et al. |
| 2003/0109916 | A1 * | 6/2003 | Don Michael ............ 623/1.11 |
| 2003/0199865 | A1 | 10/2003 | Knudson et al. |
| 2003/0199917 | A1 | 10/2003 | Knudson et al. |
| 2004/0111079 | A1 | 6/2004 | Heyes et al. |
| 2004/0148005 | A1 * | 7/2004 | Heuser .................. A61F 2/07 623/1.11 |
| 2004/0243057 | A1 | 12/2004 | Vinten-Johansen |
| 2004/0255956 | A1 | 12/2004 | Vinten-Johansen |
| 2005/0070848 | A1 | 3/2005 | Kim et al. |
| 2005/0118562 | A1 | 6/2005 | Vinten-Johansen et al. |
| 2006/0030814 | A1 | 2/2006 | Valencia et al. |
| 2006/0079573 | A1 | 4/2006 | Vinten-Johansen et al. |
| 2006/0100639 | A1 | 5/2006 | Levin et al. |
| 2006/0189960 | A1 | 8/2006 | Kesten et al. |
| 2006/0205671 | A1 | 9/2006 | Vinten-Johansen |
| 2007/0010847 | A1 | 1/2007 | Pepper |
| 2007/0129752 | A1 | 6/2007 | Webler et al. |
| 2007/0142818 | A1 | 6/2007 | Webler et al. |
| 2007/0160645 | A1 | 7/2007 | Vinten-Johansen |
| 2008/0097383 | A1 | 4/2008 | Vinten-Johansen |
| 2008/0097385 | A1 | 4/2008 | Vinten-Johansen et al. |
| 2009/0018498 | A1 | 1/2009 | Chiu et al. |
| 2010/0082012 | A1 | 4/2010 | Hattangadi et al. |

OTHER PUBLICATIONS

ISR/WO for PCT/US2010/033270 dated Jul. 9, 2010.

Poppenga et al., "Assessment of Potential Therapies for Acute T-2 Toxicosis in the Rat," 1987, Toxicon, vol. 25, No. 5, pp. 537-546, Department of Veterinary Biosciences, University of Illinois, Urbana, IL 61801, U.S.A.

Zhao, "Ischemic Postconditioning as a Novel Avenue to Protect Against Brain Injury After Stroke" Journal of Cerebral Blood Flow & Metabolism (2009) 29, 873-885, Department of Neurosurgery, Stanford University School of Medicine, Stanford, California, U.S.A.

Jennings, R.B., Murry C.E., Reimer K.A., "Preconditioning Mycocardium with Ischemia", Cardiovasc Drugs Therapy, 1991; 5:933-938.

L. G.C., Vasquez, J.A., Gallagher, K.P., Lucchessi, B.R., "Myocardial Protection With Preconditioning". Circulation, Journal of the American Heart Association, 1990; 82:609-619.

Murry C.E., Jennings, R.B., Reimer K.A., Preconditioning With Ischemia: A Delay of Lethal Cell Injury in Ischemic Myocardium. Circulation, Journal of the American Heart Association, 1986; 74: 1124-1136.

Zhao, Q.Z., Corvea, J.S., Halkos M.E., Kerendi, F. Wang N.P., Guyton R.A. et al., "Inhibition of Myocardial Injury by Ischemic Postconditioning During Reperfusion: Comparison With Ischemic Preconditioning". Am J. Physiol Heart Circ Physiol 285, Apr. 2003; H579-H588.

Yang, X.M., Proctor, J.B., Cui, I. Krieg, T., Downey, J.M., Cohen, M.V., "Multiple Brief Coronary Occlusions During Early Reperfusion Protect Rabbit Hearts by Targeting Cell Signaling Pathways". J Am. Coll. of Cardiology, 2004; 44; 110-1110.

Tsang, A., Hausenloy, D.J., Mocanu, M.M., Yellon, D.M., "Postconditioning: A Form of "Modified Reperfusion" Protects the Myocardium by Activating the Phosphatidylinositol 3-Kinase-Akt Pathway". Circulation Research, 2004; 95; 230-232.

Kin, H., Zhao, Z.Q., Sun, H.Y., Wang, N.P., Corvera, J.S., Halkos, H.E., et al. "Postconditioning Attenuates Myocardial Ischemia-Reperfusion Injury by Inhibiting Events in the Early Minutes of Reperfusion". Cardiovascular Research, 2004; 62; 74-85.

Yellon, D.M., Hausenloy, D.J., "Mycardial Reperfusion Injury". New England Journal of Medicine, 2007; 357; 1121-1135.

Staat, P., Gilles, R., Christophe, P., et al. "Postconditioning the Human heart". Circulation, Journal of the American Heart Association, 2005; 112; 2143-2148.

Piot, C. et al. "Effect of Cyclosporine on Reperfusion Injury in Acute Myocardial Infraction". New England Journal of Medicine, 2008; 359; 473-481.

Dirkson, M.T., Laarman, G.J., et al. "Reperfusion Injury in Humans: A Review of Clinical Trials on Reperfusion Injury Inhibitory Strategies". Cardiovascular Research, 2007; 74; 343-355.

Hanssen, H.J.L., Koole, L.H. "Heparin-Releasing Intravascular Guidewires". Medical Device Technology, Sep. 2002.

Peerlings, C.C.L., Hanseen, H.H.L, Bevers, R.T.J., et al. "Heparin Release From Slippery-When-Wet Guide Wires for Intravascular Use". Wiley Periodicals, 2002.

* cited by examiner

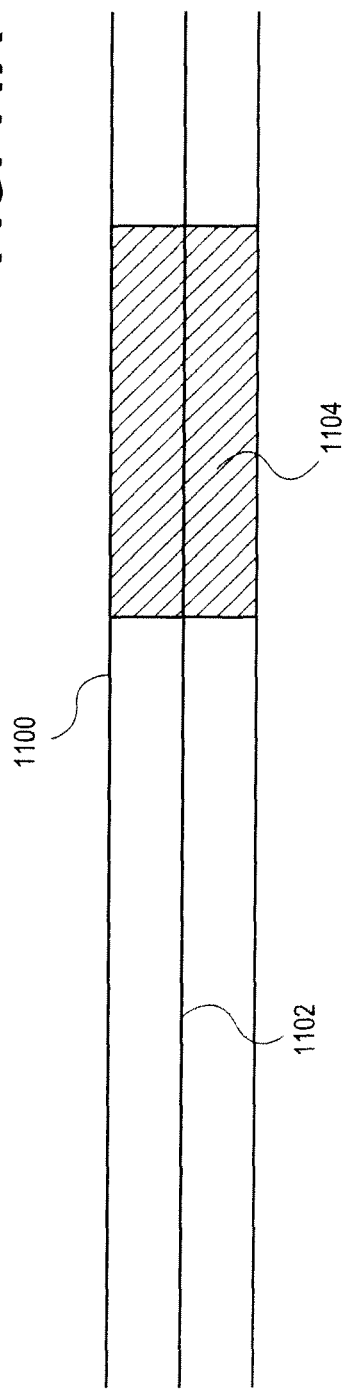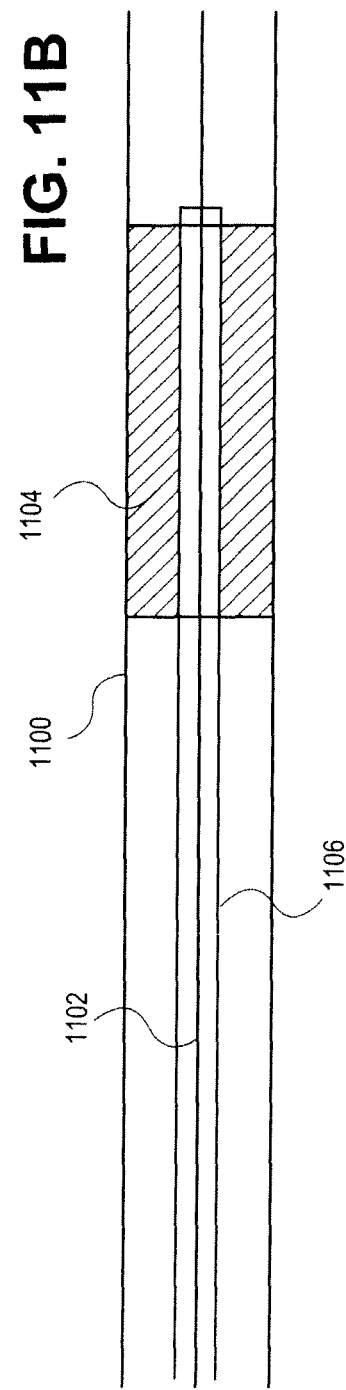

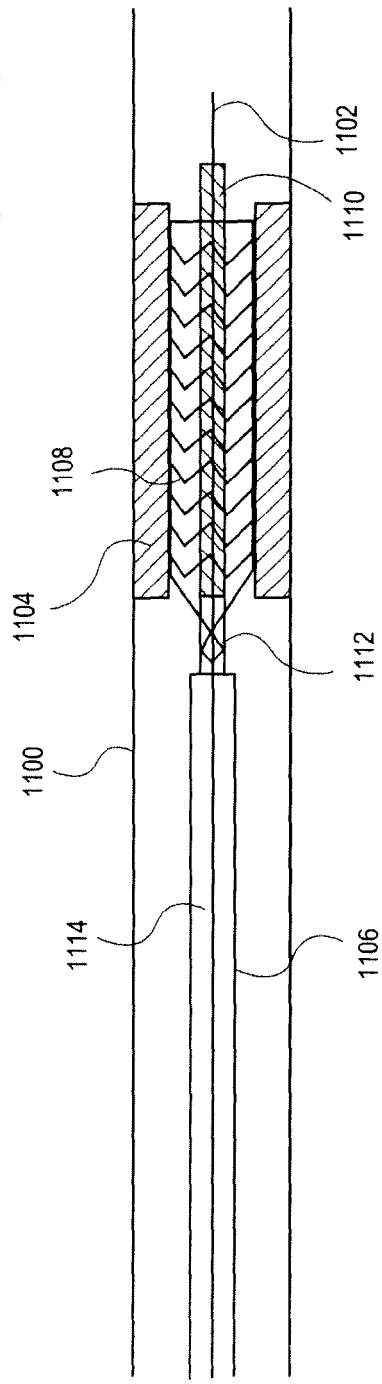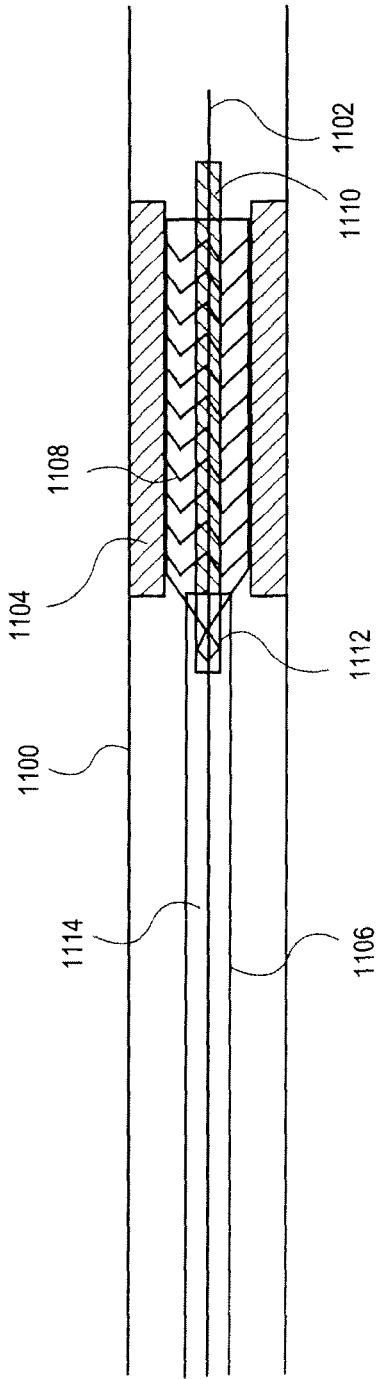

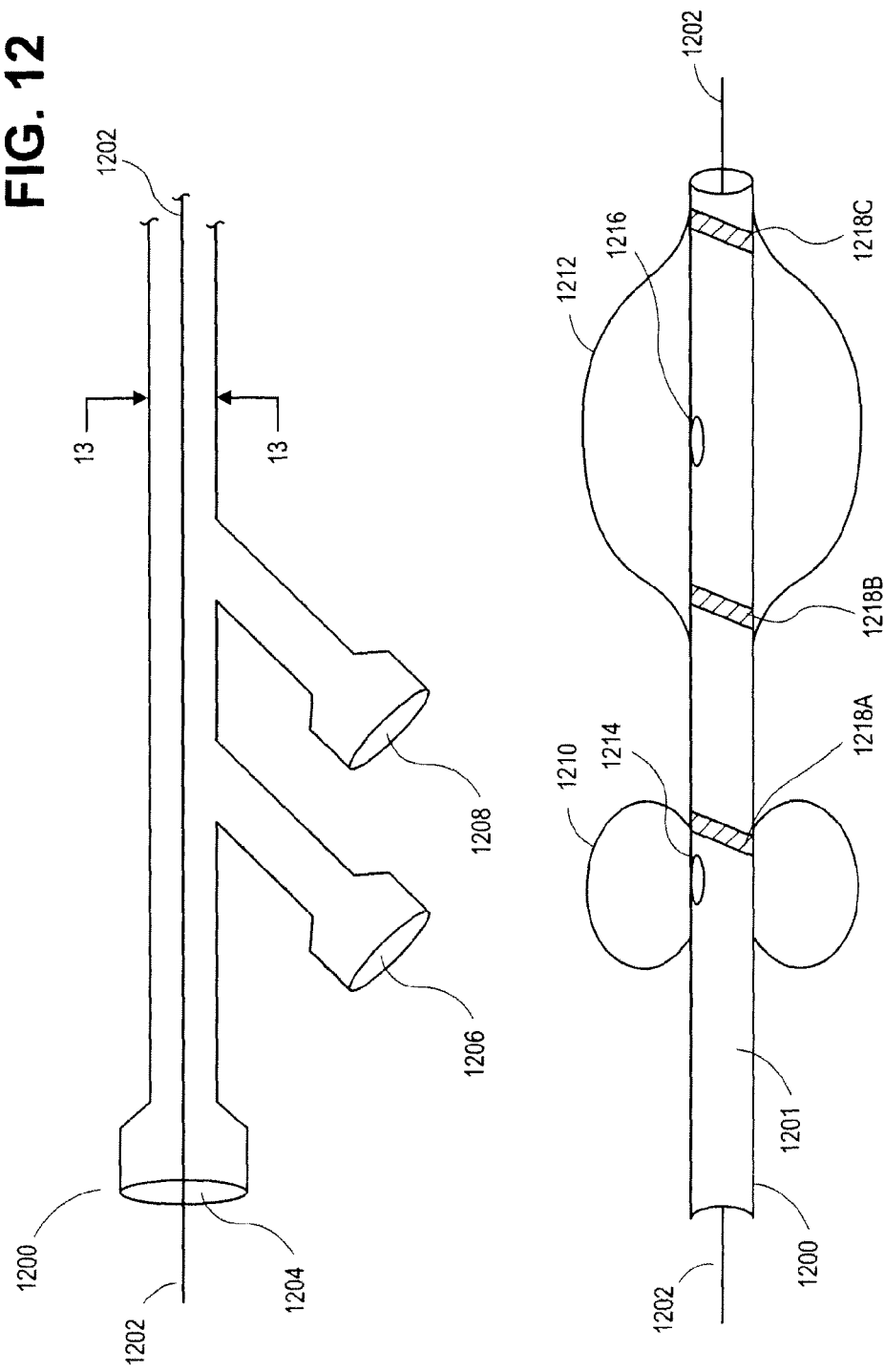

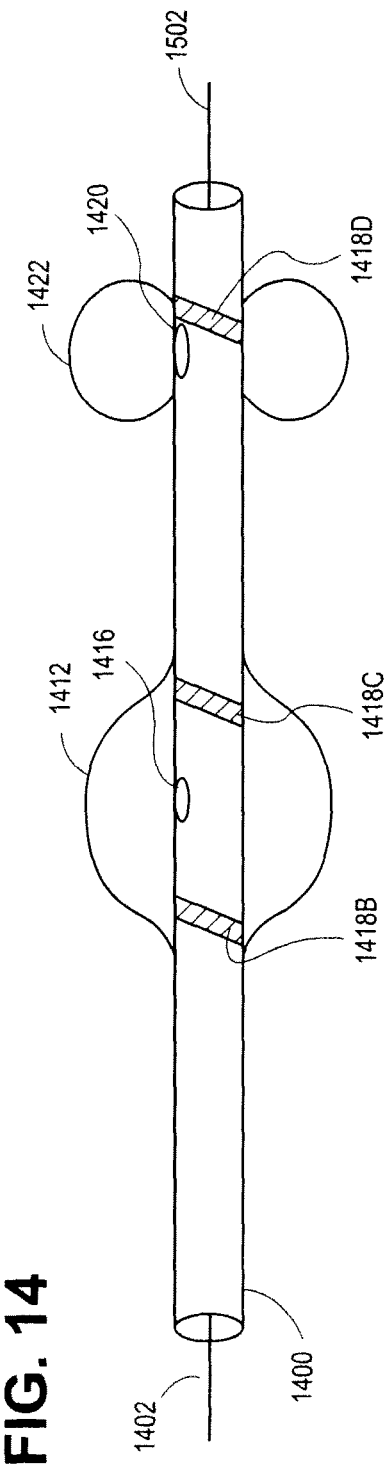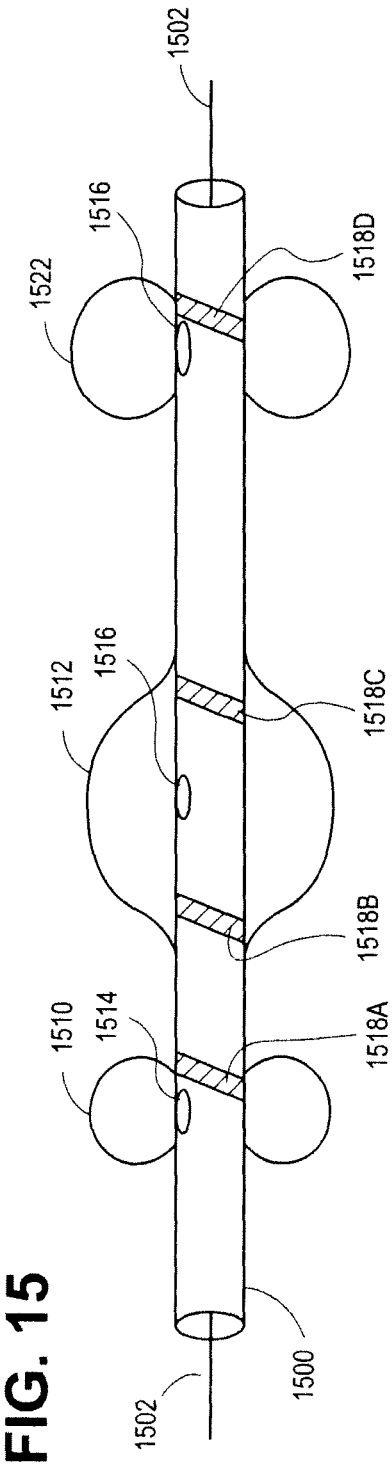

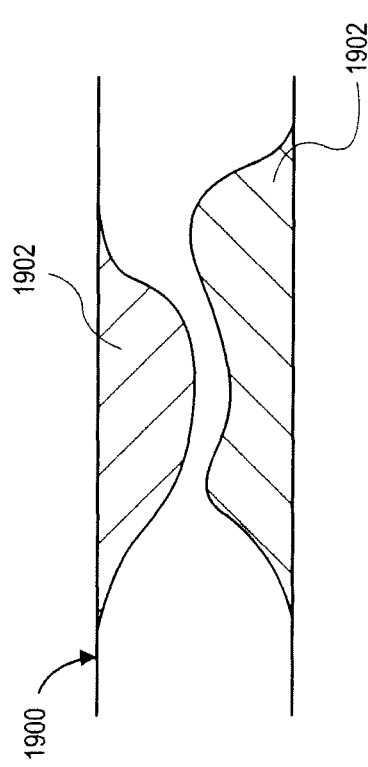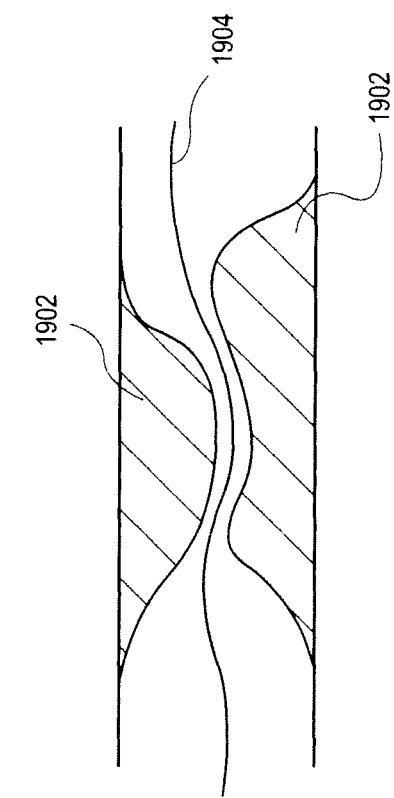

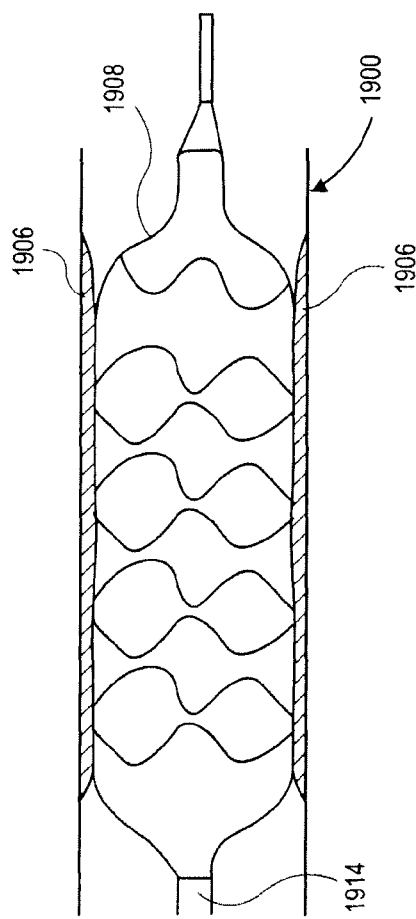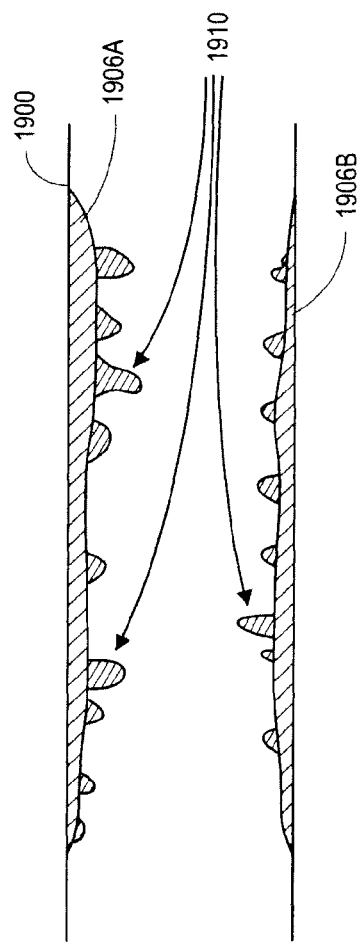

REPERFUSION INJURY DEVICES

FIELD

The present invention relates generally to medical devices, and more particularly to devices for use in reperfusion injury recovery.

BACKGROUND OF THE INVENTION

As a consequence of an ischemic myocardial event, blood supply distal to an arterial occlusion is significantly diminished. The resulting deprivation of oxygen places this tissue at risk of necrosis. The standard of care for ischemic events is urgent revascularization of the occluded artery, which is commonly performed by minimally invasive catheterization followed by angioplasty, in order dilate the ischemic blockage and fully restore the supply of the blood to the tissue.

However, restoration of blood to the tissue can result in a cascade of metabolic and inflammatory responses which can lead to the necrosis of potentially salvageable myocardium despite the restitution of adequate blood supply. This reperfusion injury significantly extends the size of the infarct, and leads to increased morbidity and mortality. A possible way to avoid this reperfusion injury is to control the flow of blood to the distal tissue following reperfusion, which may mitigate the metabolic and inflammatory response of ischemic issue when being reperfused. This may be accomplished by initially crossing the ischemic occlusion with a guidewire. A balloon or stent delivery system is then delivered across the occlusion the guidewire. The balloon or stent is deployed to dilate the vessel occlusion and restore the blood flow to the distal vessel. However, rather than maintaining the blood flow in a constant manner, it is contemplated that a more efficacious approach is to restore the blood in an intermittent fashion. In this way, the reperfused tissue will be oxygenated gradually, which will mitigate the deleterious effects of reperfusion. This will in turn maximize the tissue viability post-procedurally.

In addition, after deployment of a stent or balloon within the ischemic region, there may be thrombus generated, which is released into the blood stream. Generally, the thrombus will be carried to a distal region of the vasculature, but in some cases it may remain near the lesion or in a location that is proximal to a vessel bifurcation that supplies significant blood to heart tissue. When the thrombus remains in a more proximal location within the vessel, it presents an increased probabilistic risk of occluding the vessel and forming another ischemic event. This risk can be mitigated by displacing the thrombus to more and more distal regions of the vasculature, so that when it does occlude a vessel it will generally be a much smaller vessel that is less significant in terms of maintaining tissue viability.

Therefore, there exists a need for medical devices that are capable restoring blood flow after an ischemic in an intermittent and gradual fashion. In addition, there also exists a need for medical devices that are capable of forcing thrombotic particles into more distal regions of the vasculature to avoid ischemic events that compromise large areas of cardiac tissue.

SUMMARY OF THE INVENTION

The invention is directed to catheters that are used to perform reperfusion therapy. In a first embodiment, a reperfusion catheter of the invention generally comprises an outer member and an inner member, with the inner member having a valve and an expandable stent. In addition, the inner member is slidably disposed within the outer member when the valve is in the opened position. Furthermore, the valve is capable of an expansion that blocks blood flow past the valve when in the opened position. In one embodiment of a method of the invention, a reperfusion catheter of the first embodiment is introduced into a patient's body lumen and advanced to an occlusion in the body lumen. Blood is allowed to flow from a proximal side of the body lumen to a distal side of the body lumen. In addition, the blood flow is prevented to flow past the valve by expanding the valve such that an edge of the valve is in contact with the wall of the body lumen In second embodiment of the invention, a reperfusion catheter generally comprises an inner member, an expandable stent, and an outer member. In this embodiment, the inner member has a proximal shaft, distal shaft, and a guidewire lumen, with the distal shaft includes an inlet hole, a distal port, a fluid lumen coupling the inlet hole and the distal port, with the inlet hole in fluid communication with the distal port. The expandable stent is on the distal shaft and is located between the inlet hole and the distal port. Furthermore, the outer member is moveable relative to the inner member and the expandable stent, with the outer member having an inner lumen capable of sliding over the inner member and the expandable stent. In one embodiment of a method of the invention, a reperfusion catheter of the second embodiment is introduced into a patient's body lumen. The reperfusion catheter is advanced to an occlusion in the body lumen. The method further allows blood in a proximal side of the body lumen to flow through the inlet hole and the fluid lumen to a distal side of the occlusion and prevents the blood to flow into the inlet hole In a third embodiment of the invention, a reperfusion catheter generally comprises a shaft including a first occlusion lumen, a first occlusion opening, an angioplasty lumen, and an angioplasty opening. This reperfusion catheter further comprises a first occlusion balloon coupled to the shaft, the first occlusion balloon in fluid communication with the first occlusion lumen via the first occlusion opening, and an angioplasty balloon coupled to the shaft, the angioplasty balloon in fluid communication with the angioplasty via the angioplasty opening. In one embodiment of a method of the invention, a reperfusion catheter of the third embodiment is introduced into a patient's body lumen. The method advances the catheter to an occlusion in the body lumen and creates an opening in the body lumen by expanding the angioplasty balloon. The method further performs reperfusion therapy with the first occlusion balloon.

In a fourth embodiment of the invention, a reperfusion catheter generally comprises a shaft, a first expandable member and a second expandable member. The shaft includes a first and second lumen and a first and second opening. The first expandable member is coupled to the shaft, with the first expandable member in fluid communication with the first lumen via the first opening. The second expandable member is coupled to the shaft and distal to the first expandable member, with the second expandable member in fluid communication with the second fluid lumen via the second opening. In one embodiment of a method of the invention, a reperfusion catheter of the fourth embodiment is introduced into a patient's body lumen and plunges blood in the body lumen.

In a fifth embodiment of the invention, a reperfusion catheter generally comprises an occlusive catheter and a main catheter. The occlusive catheter has a catheter body, a fluid port, a connecting lumen, occlusive balloon, and catheter lumen, where the occlusive balloon is in fluid communication with the fluid port via the connecting lumen. The main catheter has an expandable member, with the main catheter slidably disposed within the catheter lumen. In one embodiment of a method of the invention, a reperfusion catheter of the fifth embodiment is introduced into a patient's body lumen and advanced to an occlusion in the body lumen. The method further creates an opening in the occlusion in the body lumen with the main catheter and performs reperfusion therapy with the occlusive catheter.

In a sixth embodiment of the invention, a reperfusion catheter generally comprises a shaft, an inner and outer balloon. The shaft includes a first and second lumen and a first and second opening. The outer balloon is coupled to the shaft, with the outside balloon in fluid communication with the first lumen via the first opening. The inner balloon is coupled to the shaft and inside the outer balloon, the second expandable member in fluid communication with the second lumen via the second opening. In one embodiment of a method of the invention, a reperfusion catheter of the sixth embodiment is introduced into a patient's body lumen and advanced in the body lumen. The method further creates an opening in the body lumen by expanding the outer balloon. The method deflates the outer balloon and performs reperfusion therapy with the outer balloon.

BRIEF DESCRIPTION OF THE DRAWINGS

FIGS. 11A-D illustrate the use of the catheter of FIG. 8 in the method of FIG. 10 to reduce reperfusion injury.

FIG. 12 is an elevational view of a third reperfusion catheter employing features of the invention, with the occlusion balloon proximal to the angioplasty balloon.

FIG. 14 is an elevational view of the third reperfusion catheter employing features of the invention, with the occlusion balloon distal to the angioplasty balloon.

FIG. 15 is an elevational view of the third reperfusion catheter employing features of the invention, with two occlusion balloons.

FIGS. 19A-D illustrates treating a vessel narrowing caused by an ischemic event.

DETAILED DESCRIPTION OF THE PREFERRED EMBODIMENTS

First Reperfusion Catheter

Figure 1:
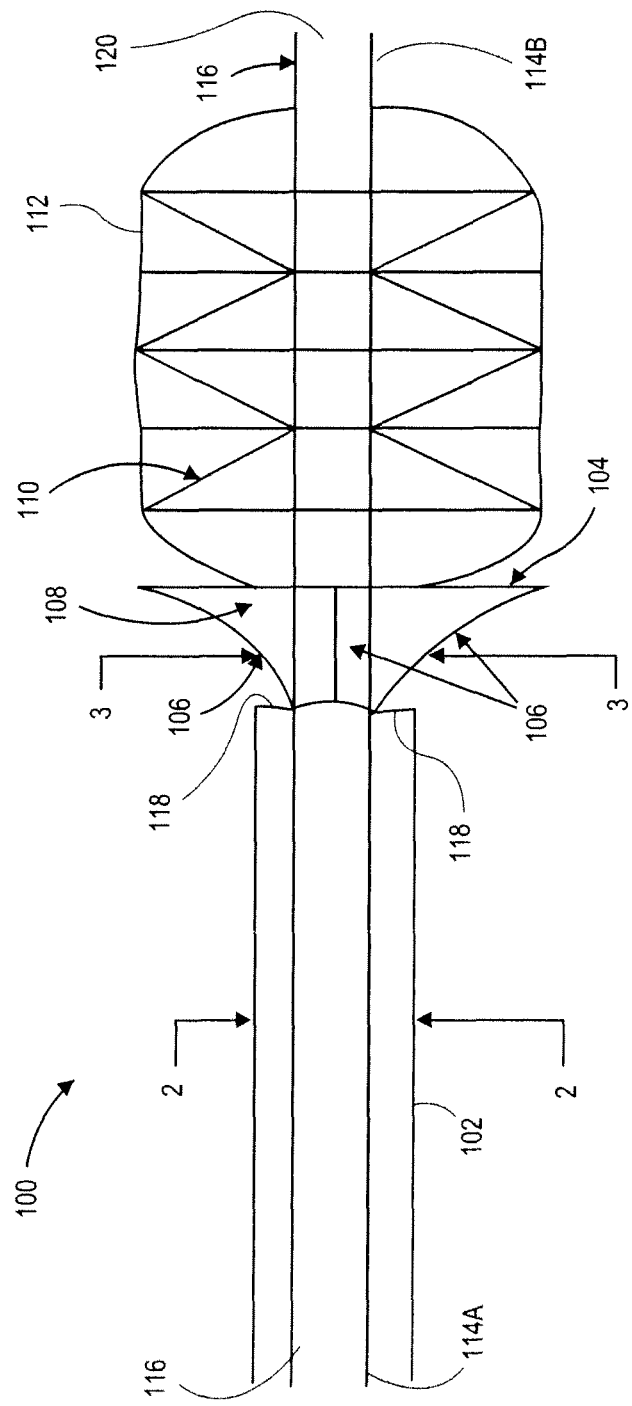
FIG. 1 is an elevational view of a reperfusion catheter 100 embodying features of the invention.

FIG. 1 is an elevational view of a reperfusion catheter 100, embodying features of the invention, generally comprising an inner member 116 and an outer member 102 that is slidably disposed relative to the inner member 116. In one embodiment, catheter 100 is capable of being delivered over a guidewire through the patient's anatomy. In one embodiment, catheter 100 is a Percutaneous Transluminal Coronary Angioplasty (PTCA) catheter having an inflatable balloon and crimped stent at distal end 114E on inner member 116 and a blood controlling mechanism that can be either proximal or distal to the stent/balloon assembly. The blood controlling mechanism can be used to control perfusion prior to the re-establishment of full blood flow. In one embodiment, blood controlling mechanism includes an expandable valve 104, which is described in greater detail below. In most embodiments of this catheter and other catheters described herein, blood is the fluid being used. In alternative embodiments, fluid other than blood can be used.

The inner member 116 can includes a proximal end 114A, distal end 114B, expandable stent 110, balloon 112, valve 104, and a guidewire 124. Proximal end 114A is proximal to valve 104 and couples to distal end 114B. The guidewire 124 runs the length of proximal 114A and distal 114B ends. In one embodiment, reperfusion catheter 100 includes radio-opaque markers that are used to locate one or more of the different components of reperfusion catheter 100. For example and in one embodiment, the one or more radio-opaque markers are markers known in the art and are used to locate the proximal 114A and distal 114B ends of the reperfusion catheter 100.

In one embodiment, valve 104 is a nitinol umbrella valve comprising of a non-porous biocompatible material. In this embodiment, valve 104 has a nitinol umbrella cage 106 covered with material 108, which can block blood flow. While in one embodiment, the material 108 of valve 104 can be polytetrafluoroethylene (PTFE), in alternate embodiments, valve 104 can consist of different materials (polyaminde, polyurethane, polyester, polyethylene terephthalant (PET), or other suitable material known in the art). In addition, valve 104 can be in an open or closed position. In this embodiment, the diameter of valve 104 in the close position is smaller than the diameter of the stent 110 when unexpanded or expanded. In one embodiment, a closed valve 104 has diameter 0.1-2 mm smaller than the diameter of stent 110. This allows the blood to flow around valve 104 to induce perfusion. In the opened position, valve 104 expands to have a diameter such that the edges of valve 104 are in substantial contact with the vessel walls, thus blocking the blood flow past valve 104.

Balloon 112 is capable of being inflated and deflated for reperfusion as is known in the art. Stent 110 is capable of expanding to stent an occlusion in a vessel as is known in the art. Balloon 112 can be used to expand the stent 110 by inflation of the balloon 112. In one embodiment, inflating and deflating balloon 112 to expand stent 110 closes a passage in a blocked vessel and allows the blood to flow through the vessel. Once the passage is opened in the blocked vessel, blood flow for reperfusion is controlled using valve 104.

In the embodiment of FIG. 1, outer member 102 includes an inner lumen 118 that is capable of sliding over the inner member 116 and coming into contact with valve 104. In one embodiment, the inner lumen 118 has a diameter slightly larger than the diameter of shaft 114A-B and the undeployed diameters of valve 104, stent 110, and balloon 112. In one embodiment, sliding the outer member 102 relative to the valve 104 opens the valve and stops the blood flow through the vessel. In one embodiment, valve 104 opens by retracting the outer member 102 relative to the valve 104, which self-expands and hence the diameter of valve 104 increases to block the blood flow. Conversely, outer member 102 can be slid distally to retract the valve 104, thus closing the valve 104. Closing valve 104 allows blood to flow through the vessel.

The catheter 100 may be fabricated using materials and processes that are well known in the art of medical device catheters. For example, and in one embodiment, the catheter 100 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density.

Figure 2:
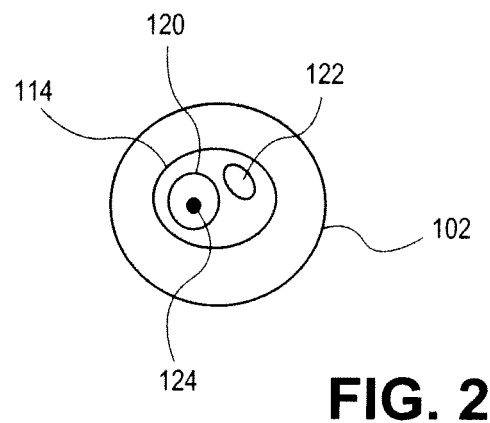
FIGS. 2 and 3 are transverse cross sectional views of the catheter of FIG. 1, taken along lines 2-2 and 3-3, respectively.
Figure 3:
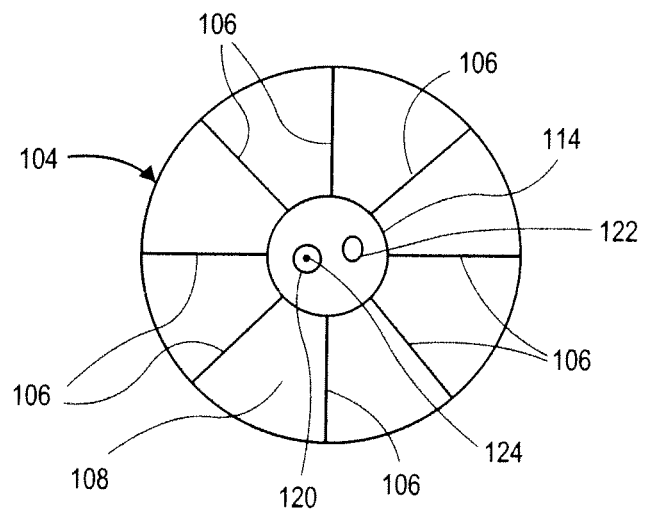

FIGS. 2 and 3 are transverse cross sectional views of the catheter 100 of FIG. 1, taken along lines 2-2 and, 3-3, respectively. FIG. 2 illustrates a transverse cross sectional view of catheter 100 taken along lines 2-2 in FIG. 1. Catheter 100 includes outer member 102 and inner member 114 slidably disposed within outer member 102. Inner member 114 includes guidewire lumen 120 and inflation lumen 122. Guidewire lumen 120 includes the guidewire 124 that is capable of sliding within guidewire lumen 124. It will be appreciated that the lumens of catheter 100 may be positioned, sized, and configured in accordance with this invention such that they are capable of being used for their intended purposes as described herein. It will also be appreciated that catheter 100 may not be a solid polymer throughout the cross section as shown, but may in fact comprise several independent tubes maintained within the inner member in the desired location.

FIG. 3 illustrates a transverse cross sectional view of catheter 100 that includes inner member 114 and valve 104 in the close position taken along lines 3-3 in FIG. 1. In the embodiment of FIG. 3, valve 104 is in the closed position, which allows blood to flow past valve 104. As in FIG. 1, valve 104 can include a nitinol umbrella cage 106 covered with material 108.

Figure 4:
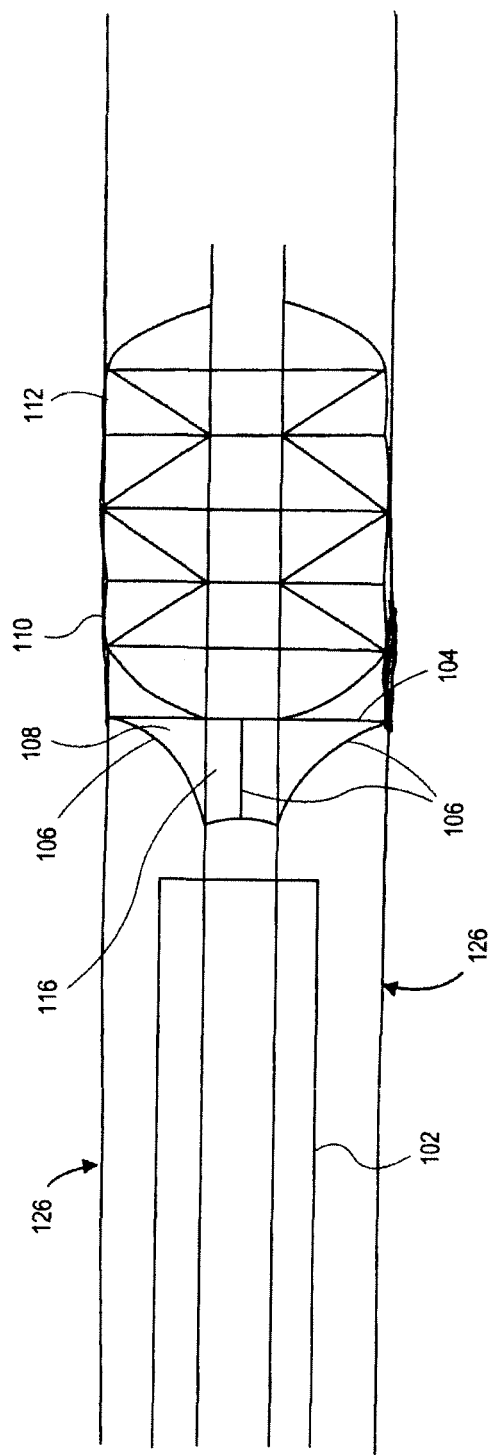
FIG. 4 illustrates the catheter of FIG. 1 with a valve opened.

FIG. 4 illustrates the catheter 100 of FIG. 1 with valve 104 opened and balloon 112 and stent 110 deployed. In this embodiment, outer member 102 opens valve 104 by unsheathing the valve 104 and allowing the valve 104 to expand such that the edges of the valve 104 are pressing against the vessel walls 126. In one embodiment, outer member 102 unsheathes the valve 104 by the outer member 102 moving proximally away from the valve 104. In this embodiment, the valve 104 is a self-expanding valve that expands upon unsheathing. In another embodiment, the valve 104 unsheathes from the outer member 102 by moving the inner member 114 structure distally away from the outer member 102. In this embodiment, the valve 104 also self-expands upon unsheathing. By opening valve 104, the blood flow from proximal to valve 104 to distal to valve 104 is either restricted or shut off. Furthermore, the deployed balloon 112 restricts blood flow as well.

Figure 5:
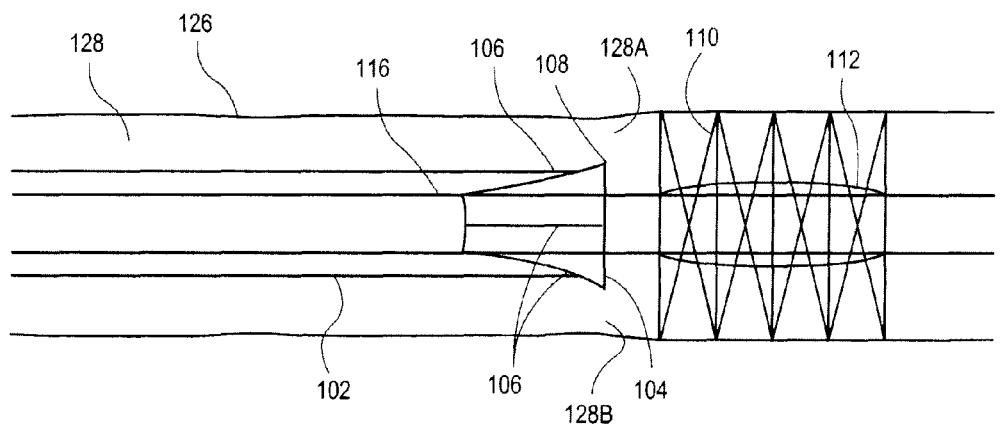
FIG. 5 illustrates the catheter of FIG. 1 with the valve close and the stent deployed.
Figure 6:
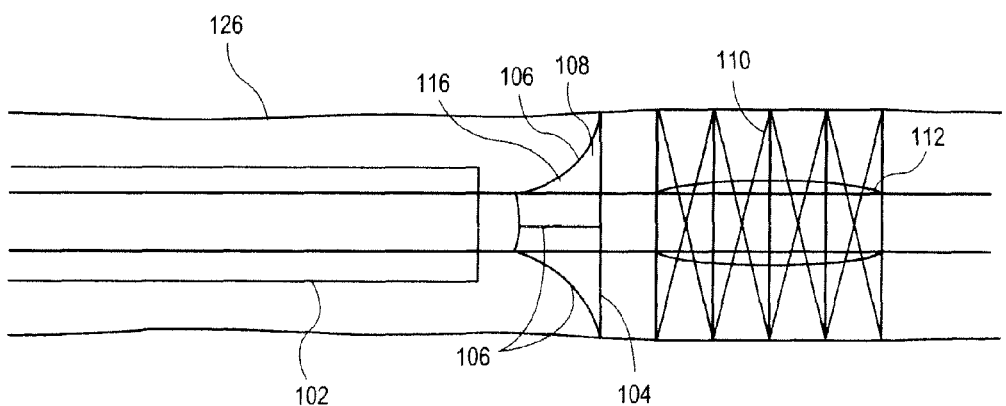
FIG. 6 illustrates the catheter of FIG. 1 with the valve opened and the stent deployed.

FIGS. 5-6 illustrate the catheter 100 deployed to effect control of reperfusion. The embodiments in FIGS. 5 and 6 illustrate valve 104 positions that are used to induce perfusion and post-conditioning ischemic events, respectively. FIG. 5 illustrates the catheter 100 with the valve 104 close and the stent 110 deployed. In this embodiment, balloon 112 is deflated allowing the blood to flow past the stent 110/balloon 112 mechanism. With the balloon 112 deflated and the stent 110 deployed, valve 104 controls the blood flow in vessel 128. In FIG. 5, outer member 102 is moved relative to valve 104 such that valve 104 is retracted into the outer member 102 in response to valve 104 moving into the outer member 102. By having outer member 102 sheathed over valve 104, the edges of valve 104 collapse away from the vessel walls 126 allowing the blood to flow around valve 104. In one embodiment, the valve 104 fully collapses into the outer member 102. In an alternate embodiment, the valve 104 partially collapses so to allow the blood to flow around the valve 104. For example and in one embodiment, with the valve 104 close, blood can flow through openings 128 A-B created between valve 104 and vessel wall 126. In this embodiment, the diameter of valve 104 is between 0.1-2 mm less than the diameter of stent 110.

FIG. 6 illustrates the catheter of FIG. 1 with the valve 104 opened and the stent 110 deployed. In this embodiment and as in FIG. 5, balloon 112 is deflated allowing the blood to flow past the stent 110/balloon 112 mechanism. With the balloon 112 deflated and the stent 110 deployed, valve 104 controls the blood flow in vessel 128. In FIG. 6, outer member 102 is slid proximally and away valve 104 and deploying valve 104. By deploying valve 104, the valve 104 expands such that the edges of valve 104 are increased and are in substantial contact with vessel walls 126, thus preventing the blood to flow around valve 104. By preventing the blood flow, valve 104 produces an ischemic event in vessel 128.

Figure 7:
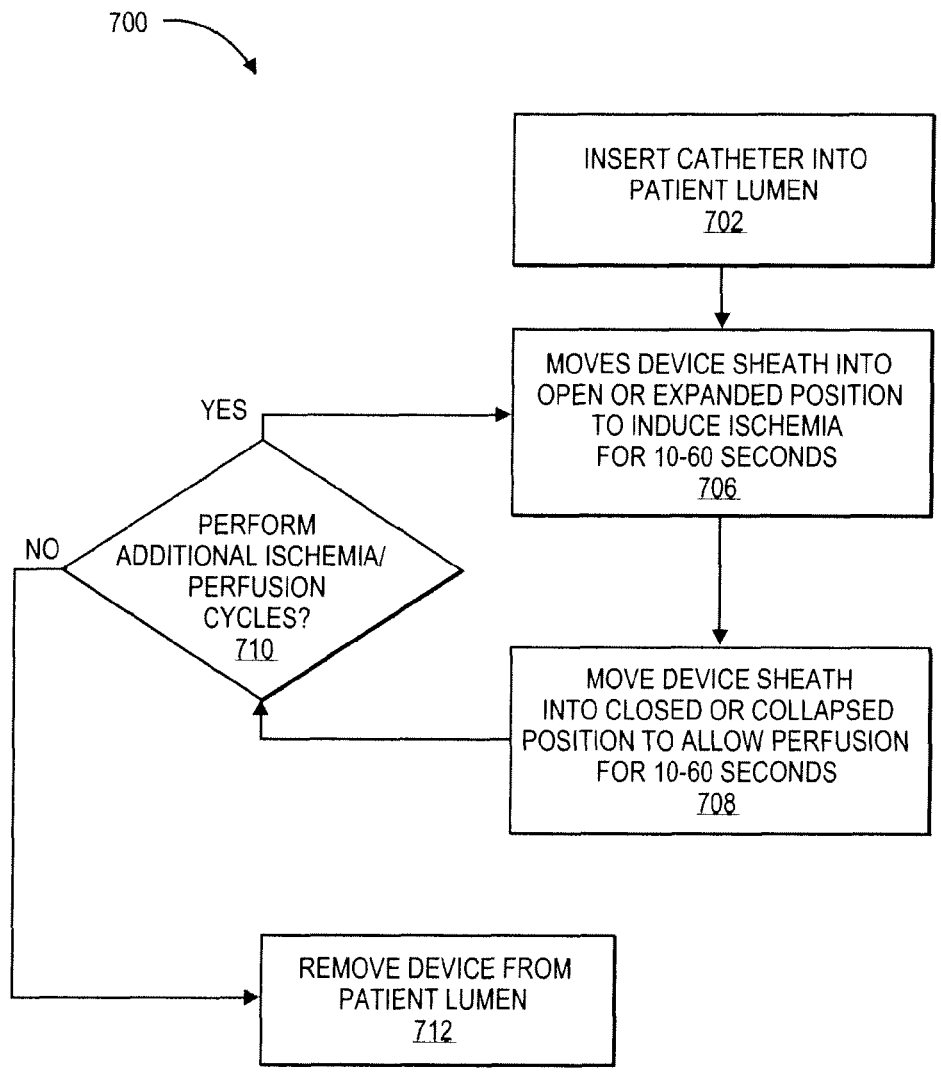
FIG. 7 is one embodiment of a method using the catheter of FIG. 1 to reduce reperfusion injury.

FIG. 7 is one embodiment of a method 700 using the catheter of FIG. 1 to reduce reperfusion injury. In FIG. 7, method 700 begins by inserting a reperfusion catheter into a patient lumen at block 702. In one embodiment, method 700 inserts catheter 100 as described in FIG. 1 above.

At block 704, method 700 positions the catheter in the vessel to effect reperfusion. In one embodiment, method 700 positions the catheter inside an ischemic blockage such that the stent and balloon can dilate that blockage. For example and in one embodiment, method 700 can use a guidewire to open a channel through the ischemic blockage and use this channel to guide the stent/balloon mechanism through the opened channel and into the ischemic blockage. Once the stent/balloon mechanism is positioned inside the ischemic blockage, method 700 opens the valve 104 to block blood flow and then dilates the ischemic blockage by inflating the balloon and/or deploying stent to create a larger opening in the ischemic blockage. In one embodiment, method 700 inflates balloon 112 and deploys stent 110 of catheter 100 within the ischemic blockage as described in FIGS. 4-6. After deploying the stent, method 700 deflates the balloon to allow blood flow past the stent/balloon mechanism.

Method 700 moves the outer member relative to the valve so as to open the valve and induce short periods of postconditioning ischemia at block 706. In one embodiment, method 700 opens the valve by retracting the outer member relative to the valve such that the edges of the valve expand and come in contact with the vessel wall, thus blocking blood flow past the valve. In one embodiment, method 700 keeps the valve in the opened position for 10-60 seconds and preferably 30 seconds. In alternative embodiment, method 700 can keep the valve opened for shorter or longer periods of time.

At block 708, method 700 closes the valve to allow the blood to flow past the valve to induce short periods of perfusion. In one embodiment, method 700 closes the valve by sliding the outer member over the valve, where the valve edges are pulled into the outer member and retract from the vessel wall and allowing blood to flow past the valve. In one embodiment, method 700 keeps the valve in the close position to perform perfusion for 10-60 seconds and preferably 30 seconds. In an alternative embodiment, method 700 can keep the valve close to perform perfusion for shorter or longer periods of time.

At block 710, method 700 determines if additional ischemia/perfusion cycles should be performed. In one embodiment, up to 3-10 cycles can be performed. If no further cycles are needed, method 700 removes the device from the patient at block 712. If further cycles are desired, execution proceeds to block 706.

In an alternative embodiment, method 700 can perform reperfusion using alternate methods. For example, and in one embodiment, method 700 partially closes the valve to provide a desired amount of blood flow; and/or opens and closes the valve on a manner to provide a specific pattern of flow (e.g., gradual increase or decrease in blood flow) that minimizes reperfusion injury.

In one embodiment, the first reperfusion catheter of FIG. 1 can include one or more mechanical and/or programmable controllers that would perform the reperfusion therapy as described above in FIG. 7.

Second Reperfusion Catheter

Figure 8:
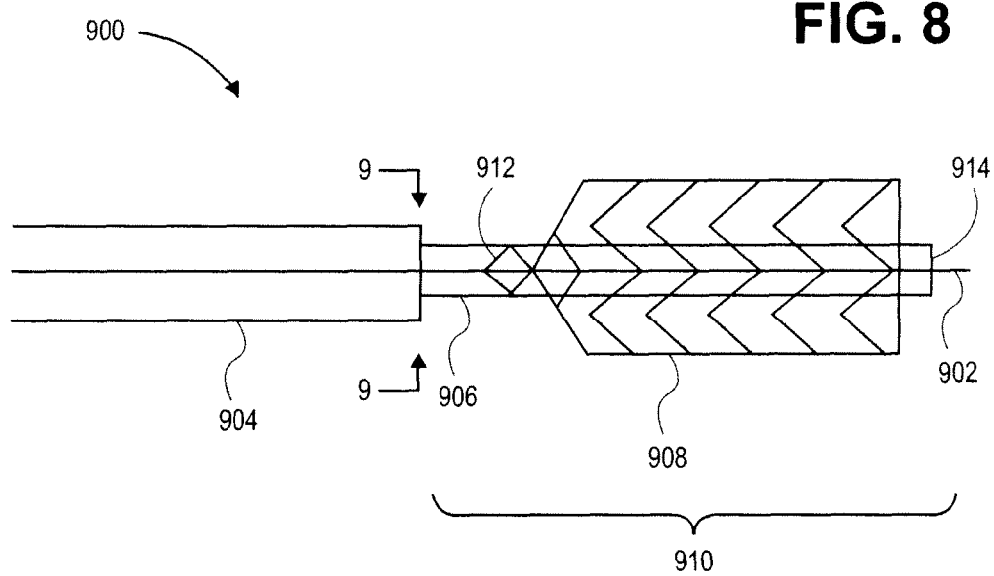
FIG. 8 is an elevational view of a second reperfusion catheter embodying features of the invention.

FIG. 8 is an elevational view of a second reperfusion catheter 900 embodying features of the invention, generally comprising a sheathed expansion member 910 that is deployable and may be recaptured by an outer member 904. In this embodiment, second reperfusion catheter 900 deploys sheathed expansion member 910 to allow blood flow through the expansion member 910. Conversely, recapturing the expansion member 910 prevents blood flow through the expansion member 910. Deploying or recapturing the expansion member 910, when the expansion member 910 is at least partially in a vascular occlusion, controls blood flow to a distal anatomy. In one embodiment, catheter 900 is capable of being delivered over a guidewire through the patient's anatomy. Thus, catheter 900 can be used for controlled reperfusion of anatomies distal to the vascular occlusion, and therefore allows for post-conditioning techniques that may improve tissue survival and viability.

In FIG. 8, sheathed expansion 910 is slidably disposed within outer member 904. Sheathed expansion 910 can include shaft 906, expandable stent 908, opening 912, port 914, and guidewire 902. In one embodiment, expandable stent 908 is a self-expandable structure, such as a self-expanding stent. The expandable part of expandable stent 908 may be formed from Nitinol, and may be recoverable from a first configuration in which the expandable stent 908 is captured in the outer member 904, to a second configuration when the outer member is retracted to expose the expandable stent 908. In one embodiment, this expandable member may be tapered bare on at least one end, and in another embodiment, may be tapered at the proximal end. In this embodiment, this tapered shape permits the expandable stent 908 to be associated with the outer member 904. In addition, this taper provides a gradual transition surface that allows the expandable stent 908 to be collapsed when the outer member 904 is advanced over the expandable stent 908. In one embodiment, the side wall of the expandable stent 908 has a polytetrafluoroethylene (PTFE) (or some other polymer known in the art) cover. In this embodiment, the cover prevents any plaque rupture from the vessel occlusion to escape into the lumen created by the expandable stent 908. Guidewire 902 runs the length of shaft 906. In one embodiment, catheter 900 includes radio-opaque markers that are used to locate one or more of the different components of catheter 900. For example and in one embodiment, the one or more radio-opaque markers are markers known in the art and are used to locate the expandable stent 908.

Opening 912 is an opening in the sheathed expansion 910 that is in fluid communication with the port 914 at the distal end of the sheathed expansion 910. In one embodiment, with the outer member 904 is moved to uncover the opening 912, blood can flow into the opening 912 through shaft 906 and out port 914. This embodiment can be used to induce periods of perfusion. In another embodiment with the outer member 904 covering or blocking the opening 912, blood flow is prevented through the sheathed expansion 910. By blocking blood flow, this embodiment is used to induce periods of post-conditioning ischemia. It will be appreciated that the shaft 906 allows for blood to flow through the shaft 906 without being lost to the surroundings immediately adjacent to the shaft 906.

The catheter 900 may be fabricated using materials and processes that are well known in the art of medical device catheters. For example, and in one embodiment, the catheter 900 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density.

Figure 9:
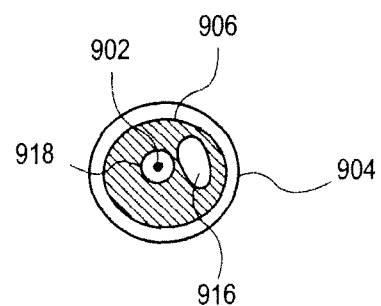
FIG. 9 is a transverse cross sectional view of the catheter of FIG. 8, taken along lines 9-9.

FIG. 9 is a transverse cross sectional view of the catheter of FIG. 8, taken along lines 9-9. In FIG. 9, the outer member 904 is slidably disposed over the shaft 906. Shaft 906 can include a fluid lumen 918, guidewire lumen 916, and the guidewire 902. In one embodiment, the fluid lumen 918 allows blood flow from the opening 912 through shaft 906 and out port 914. Guidewire lumen 916 includes the guidewire 902 that is capable of sliding within guidewire lumen 916. It will be appreciated that the lumens may be positioned, sized, and configured in accordance with this invention such that they are capable of being used for their intended purposes as described herein. It will also be appreciated that catheter 900 may not be a solid polymer throughout the cross section as shown, but may in fact comprise several independent tubes maintained within the inner member in the desired location.

Figure 10:
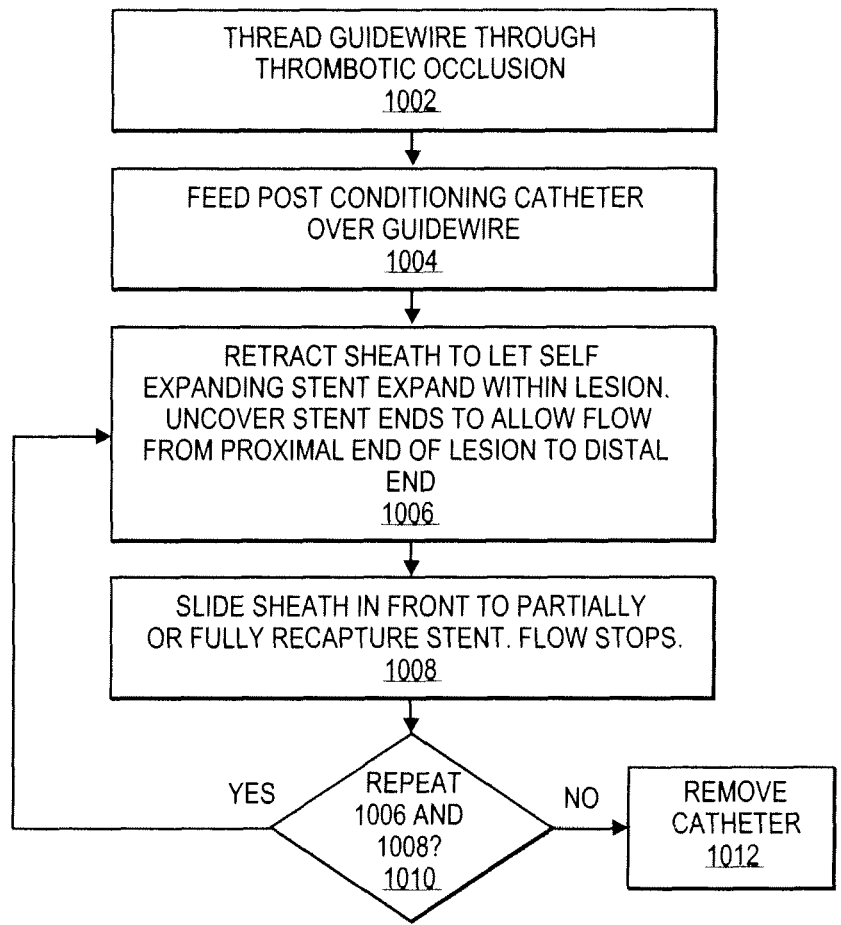
FIG. 10 is one embodiment of a method using the catheter of FIG. 8 to reduce reperfusion injury.

FIG. 10 is one embodiment of a method 1000 using the catheter 900 of FIG. 8 to reduce reperfusion injury. The discussion of FIG. 10 will refer to FIGS. 11A-D to illustrate the different blocks of method 900. FIGS. 11A-D illustrate the use of the catheter 900 of FIG. 8 in the method of FIG. 10 to reduce reperfusion injury.

In FIG. 10, method 1000 threads the catheter guidewire through the occlusion at block 1002. For example and in one embodiment, as illustrated in FIG. 11A, method 1000 threads the guidewire 1102 through an occlusion 1104 that is partially or fully blocking vessel 1100. In this embodiment, vessel 1100 is illustrated after an ischemic event. Because of the occlusion 1104, blood flow in the distal direction has been significantly slowed or stopped. By threading through the occlusion 1104, method 1000 creates an opening in the occlusion 1104 that can be used to guide other parts of the catheter into and/or through the occlusion 1104.

At block 1004, method 1000 feeds the catheter over the guidewire and through the vasculature to the site of the occlusion. In addition, method 1000 advances the catheter through the occlusion. As illustrated in FIG. 11B and in one embodiment, method 1000 advances catheter 1106 over guidewire 1102 into occlusion 1104. In one embodiment, catheter 1106 is catheter 900 as described in FIG. 8 with the outer member 904 covering the expandable stent 910. In this embodiment, the diameter of catheter 1100 is the diameter of the outer member.

Method 1000 retracts that outer member past the expandable stent and shaft opening, which allows the expandable stent to expand within the occlusion and blood to flow through the through the shaft and out the distal port. As illustrated in the FIG. 11C, method 1000 retracts outer member 1114 to reveal the expandable stent 1108. In one embodiment, the expandable stent 1108 is a self-expandable stent and automatically expands after outer member 1106 is retracted past the expandable stent 1108. The expandable stent 1108 can partially or completely create an opening in the occlusion 1104. As illustrated in FIG. 11C, method 1000 has advanced the catheter 1106 past occlusion 1104 so that the end of the shaft 1110 is distal to the occlusion 1104.

Furthermore, method 1000 thus retracts the outer member past the opening in the catheter so as to allow blood to flow past the blocking occlusion. In this embodiment, the shaft opening is in fluid communication with the proximal vessel segment and the distal vessel segment is in fluid communication with the distal end of the catheter shaft. For example, and in one embodiment, method 1000 retracts outer member 1114 of catheter 1106 past the opening 1112 as illustrated in FIG. 11C. This allows the blood to flow into the opening 1112, through a fluid lumen in shaft 1110 and out a port at the distal end of shaft 1110. By allowing the blood to flow past the occlusion, this embodiment can be used to induce periods of perfusion. In one embodiment, method 1000 allows blood flow for 10-60 seconds and preferably 30 seconds. In alternative embodiment, method 1000 can allow blood flow to induce perfusion for shorter or longer periods of time.

At block 1008, method 1000 slides the outer member to cover the shaft opening, so as to block blood flow into the opening. By blocking blood flow into the shaft opening, method 1000 can induce periods of post-conditioning ischemia. In one embodiment, method 1000 induces ischemia for 10-60 seconds and preferably 30 seconds. In alternative embodiment, method 1000 induces ischemia for shorter or longer periods of time.

As illustrated in FIG. 11D, method 1000 slides outer member 1114 of catheter 1106 past opening 1106 to block the blood flow into the opening 1112. In one embodiment, method 1000 slides outer member 1114 such that the opening 1112 is blocked, but the expandable stent 1108 is not retracted. In this embodiment, method 1000 can slide the outer member 1114 can be contact with the tapered proximal end of the expandable stent 1108.

Method 1000 determines if blocks 1006 and 1008 should be repeated at block 1010. In one embodiment, blocks 1006 and 1008 are repeated 3-10 times. In alternate embodiments, blocks 1006 and 1008 can be repeated less or more times. By retracting the outer member to restore blood flow and advancing the outer member to stop the blood flow, an operator can control the rate and duration of reperfusion. A variety of reperfusion profiles can be achieved in this way.

If method 1000 determines these blocks should be repeated, method 1000 proceeds to block 1006. If not, method 1000 removes the catheter and/or any other processes as needed to restore perfusion to the vessel. In one embodiment, method 1000 fully recaptures the expandable stent within the outer member and the catheter is removed from the vessel. In this embodiment, by fully recapturing the expandable stent, the catheter will be in the configuration as illustrated in FIG. 11B. The remaining occlusion can be treated using balloon angioplasty and/or stenting as known in the art. Since the distal vessel segment is reperfused prior to opening the vessel occlusion, there will be optimal vitalization of the distal tissue that was affected by the ischemic event.

In an alternative embodiment, method 1000 can perform reperfusion using alternate methods. For example, and in one embodiment, method 1000 partially opens the inlet to provide a desired amount of blood flow; and/or opens and closes the inlet on a manner to provide a specific pattern of flow (e.g., gradual increase or decrease in blood flow) that minimizes reperfusion injury.

In one embodiment, the second reperfusion catheter of FIGS. 8 and/or 9 can include one or more mechanical and/or programmable controllers that would perform the reperfusion therapy as described above in FIG. 10.

Third Reperfusion Catheter

FIG. 12 is an elevational view of a third reperfusion catheter 1200 employing features of the invention, with an occlusion balloon 1210 that can be proximal and/or distal to an angioplasty balloon 1212. In one embodiment, catheter 1200 is capable of being delivered over a guidewire through the patient's anatomy. As with the previously described reperfusion catheters, the catheter 1200 is used to treat blood vessel (arteries, etc.) that have become occluded with thrombus leading to ischemia of tissue distal to the occlusion. For example, an ischemic myocardium that is distal to the occluded coronary artery at a site of thrombus formed secondary is vulnerable to the rupture of a lesion.

Catheter 1200 generally can include ports 1204, 1206, and 1208 for control of components at the distal end of catheter 1200, a shaft 1201, a guidewire 1202 running the length of catheter 1200, an occlusive balloon 1210, and an angioplasty balloon 1212 at the distal end of catheter 1200. Therapeutic port 1204 is used to deliver therapeutic agents distal to the occlusion. Occlusive port 1206 is used to control the occlusive balloon 1210. In one embodiment, the occlusive balloon 1210 is controlled through an occlusive opening 1214 in catheter 1200. In one embodiment, occlusive balloon 1210 is similar to a Balloon Occlusion Infusion Catheter (BOIC) balloon with a diameter appropriate for occlusion of a primary artery and is proximal to angioplasty balloon 1212. Angioplasty balloon port 1208 is used to control the angioplasty balloon 1212. In one embodiment, the angioplasty balloon 1212 is controlled through an angioplasty opening 1216 in catheter 1200. In one embodiment, the angioplasty balloon 1212 is an angioplasty balloon as known in the art. The balloons 1210 and/or 1212 can be controlled with fluid, air, carbon dioxide, or another mechanism for controlling medical vessel balloons known in the art.

In addition, catheter 1200 includes radio-opaque markers 1218A-C that are used to locate the occlusive 1210 and angioplasty 1212 balloons. In one embodiment, radio-opaque markers 1218A-C are one as is known in the art. In one embodiment, one radio-opaque marker 1218A is used to locate the occlusive balloon 1210 within a blood vessel. Furthermore, radio-opaque markers 1218B-C are used to locate the proximal and distal ends of angioplasty balloon 1212, respectively.

The catheter 1200 may be fabricated using materials and processes that are well known in the art of medical device catheters. For example, and in one embodiment, the catheter 1200 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density. In addition, the balloons of catheter 1200 may be formed from suitable materials, such as polyvinylchloride, polyethylene terephthalate, nylon, and Pebax™.

In one embodiment, the balloon 1210 is able to occlude the lumen of an artery or other vessel (e.g., circular, eccentric, irregular, etc.) and block flow through this artery. In one embodiment, the balloon 1210 is made of compliant material that will conform to the shape of the artery and minimizing stretching or trauma to the artery.

In one embodiment, the guidewire 1202 runs the length of the catheter 1200 by being introduced into the catheter 1200 through therapeutic port 1204. In another embodiment, the guidewire 1202 is introduced in another port (not illustrated) along the shaft 1201 of catheter 1200. For example and in one embodiment, the guidewire is introduced through a port that is proximal to the balloon 1210 and 1212.

Figure 13A:
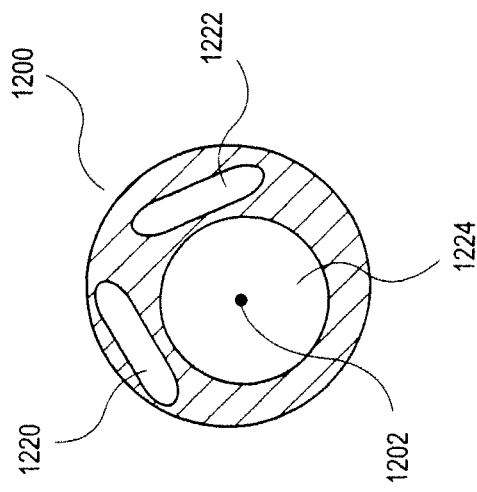
FIGS. 13A-B are transverse cross sectional views of two different embodiments of the catheter of FIG. 12, taken along lines 13-13.
Figure 13B:
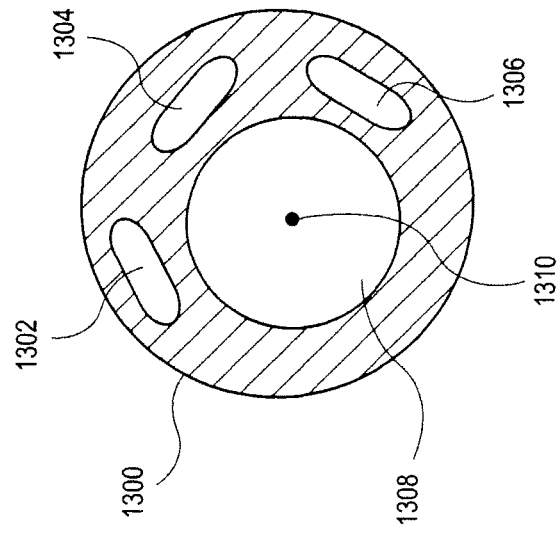

FIGS. 13A-B are transverse cross sectional views of the catheter of FIG. 12, taken along lines 13-13. In FIG. 13A, catheter 1200 can include three lumens: lumen 1220 for controlling the occlusive balloon 1210; lumen 1222 for controlling the angioplasty balloon 1212; and a guidewire lumen 1224. In one embodiment, a guidewire 1202 is capable of sliding through the guidewire lumen 1224.

The catheter 1300 illustrated in FIG. 13B is similar to the catheter 1200 illustrated in FIG. 13A, except that catheter 1300 includes an extra lumen that can be used to deliver therapeutic agents or to control a second occlusive balloon (not shown). Catheter 1300 can include an occlusive balloon lumen 1302, an angioplasty balloon 1304, guidewire lumen 1308, and auxiliary lumen 1306. Occlusive balloon lumen 1302 is used for controlling the occlusive balloon. The angioplasty balloon 1304 is used for controlling the angioplasty balloon. A guidewire 1210 is capable of sliding through the guidewire lumen 1308. Auxiliary lumen 1306 can be used to control a second occlusive balloon (as illustrated in FIG. 15 below) or can be used to deliver therapeutic agents distal to the occlusion.

FIG. 14 is an elevational view of the third reperfusion catheter 1400 employing features of the invention, with the occlusion balloon is distal to the angioplasty balloon. Catheter 1400 generally can include a guidewire 1202 running the length of catheter 1400, an occlusive balloon 1422, and an angioplasty balloon 1412. In this embodiment, occlusive balloon 1422 is distal to the angioplasty balloon 1412. Furthermore, catheter 1400 includes radio-opaque markers 1418B-D that are used to locate the occlusive 1422 and angioplasty 1412 balloons. In one embodiment, radio-opaque markers 1418B-D are one as is known in the art. In one embodiment, one radio-opaque marker 1418D is used to locate occlusive balloon 1422 within a blood vessel. Furthermore, radio-opaque markers 1418B-C are used to locate the proximal and distal ends of angioplasty balloon 1412, respectively.

FIG. 15 is an elevational view of the third reperfusion catheter 1500 employing features of the invention, with two occlusive balloons. Catheter 1500 generally can include a guidewire 1502 running the length of catheter 1500, a proximal occlusive balloon 1512, a distal occlusive balloon 1522, and an angioplasty balloon 1512. In this embodiment, proximal occlusive balloon 1510 is proximal and distal occlusive balloon 1522 is distal to the angioplasty balloon 1512, respectively. Furthermore, catheter 1500 includes radio-opaque markers 1518A-D that are used to locate the proximal occlusive 1510, distal occlusive 1522, and angioplasty 1512 balloons. In one embodiment, radio-opaque markers 1518A-D are ones as is known in the art. In one embodiment, radio-opaque markers 1518A and 1518D are used to locate proximal occlusive 1510 and distal occlusive 1522 balloons within a blood vessel. Furthermore, radio-opaque markers 1518B-C are used to locate the proximal and distal ends of angioplasty balloon 1512, respectively.

Figure 16:
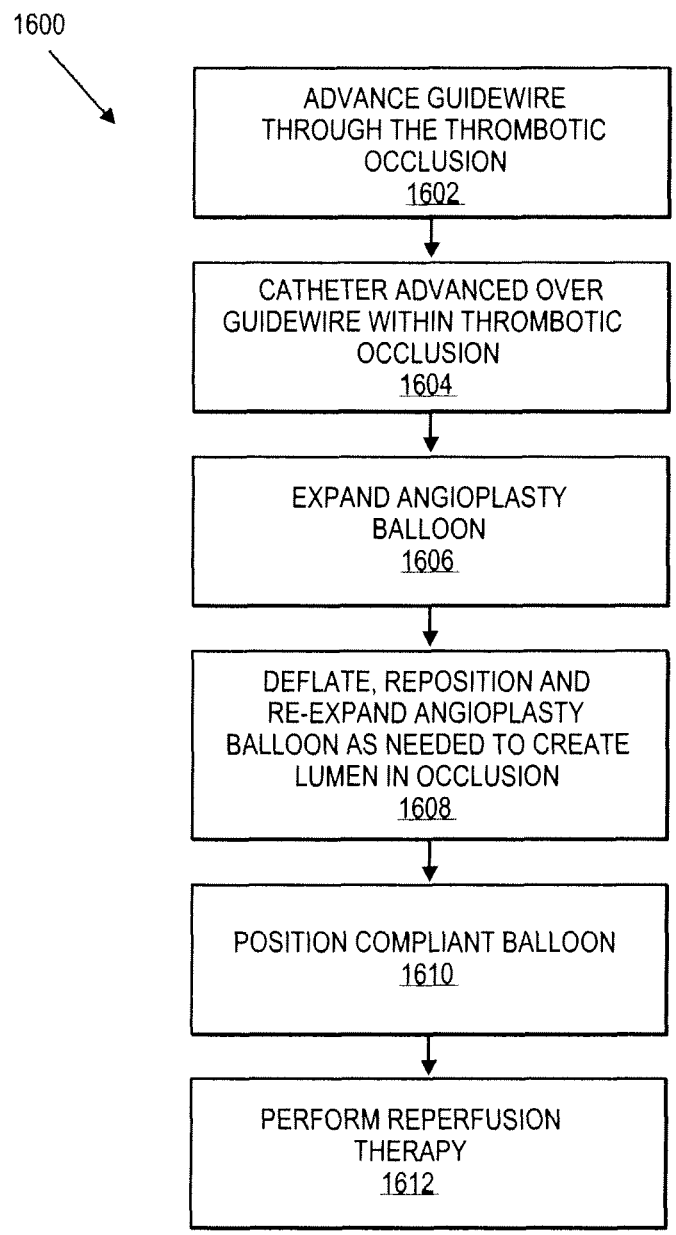
FIG. 16 is one embodiment of a method using the catheter of FIG. 12, 14, or 15 to reduce reperfusion injury.

FIG. 16 is one embodiment of a method 1600 using one of the catheter of FIG. 12, 14, or 15 to reduce reperfusion injury. In FIG. 16, at block 1602, method 1600 advances the guidewire through the thrombotic occlusion. In one embodiment, guidewire 1202, 1402, or 1502 is used to advance through the occlusion with catheter 1200, 1400, or 1500, respectively.

At block 1604, method 1600 advances the catheter over the guidewire within the thrombotic occlusion. Method 1600 expands angioplasty balloon at block 1606. In one embodiment, method 1600 expands angioplasty balloon 1212, 1412, or 1512 of catheter 1200, 1400, or 1500, respectively. In one embodiment, method 1600 uses the angioplasty balloon radio-opaque markers to position the angioplasty balloon within the occlusion.

At block 1608, method 1600 deflates angioplasty balloon. Furthermore, method 1600 repositions and re-expands angioplasty balloon as needed to create a lumen in the occlusion at block 1610. In one embodiment, method 1600 uses the angioplasty balloon radio-opaque markers to position the angioplasty balloon within the occlusion. In one embodiment, method 1600 creates a lumen over the length of the occlusion.

Method 1600 performs reperfusion therapy at block 1612. In one embodiment, an occlusive balloon is positioned in the previously occluded blood vessel proximal to, within, or distal to the site of the occlusion using an occlusive radio-opaque marker. After positioning performs reperfusion using a reperfusion methods: (a) inflate and deflate the occlusive balloon(s) to provide cyclical blood flow (the Staccato balloon method); (b) partially inflate the occlusive balloon(s) to provide a desired amount of blood flow; and/or (c) inflate and deflate the occlusive balloon(s) on a manner to provide a specific pattern of flow (e.g., gradual increase or decrease in blood flow) that minimizes reperfusion injury. Method 1600 can perform reperfusion using the proximal, distal, or both occlusive balloons.

In one embodiment, using the Staccato method mentioned above, method 1600 alternatively inflates and deflates the occlusive balloon to induce short periods of ischemia and reperfusion, respectively. In one embodiment, method 1600 inflates the occlusive balloon to affect an ischemic event. In one embodiment, method 1600 keeps the balloon inflated for 10-60 seconds and preferably 30 seconds. In alternative embodiment, method 1600 can keep the balloon inflated for shorter or longer periods of time. In addition, method 1600 deflates the balloon and/or leaves the balloon in the deflated position for 10-60 seconds and preferably 30 seconds. In alternative embodiment, method 1600 can keep the occlusive balloon deflated for shorter or longer periods of time. The inflation/deflation is repeated as necessary by method 1600. For example, and in one embodiment, method 1600 inflates and deflates the occlusive balloon as described above 3-10 times.

In one embodiment, the third reperfusion catheter of FIGS. 12, 14, and/or 15 can include a valve internal to the occlusion balloon(s) (not illustrated) which allows staged blood flow while the third reperfusion catheter is being deployed. Furthermore, in alternative embodiment, the third reperfusion catheter of FIGS. 12, 14, and/or 15 can include one or more mechanical and/or programmable controllers that would perform the reperfusion therapy as described above in FIG. 16, block 1612.

Fourth Reperfusion Catheter

Figure 17:
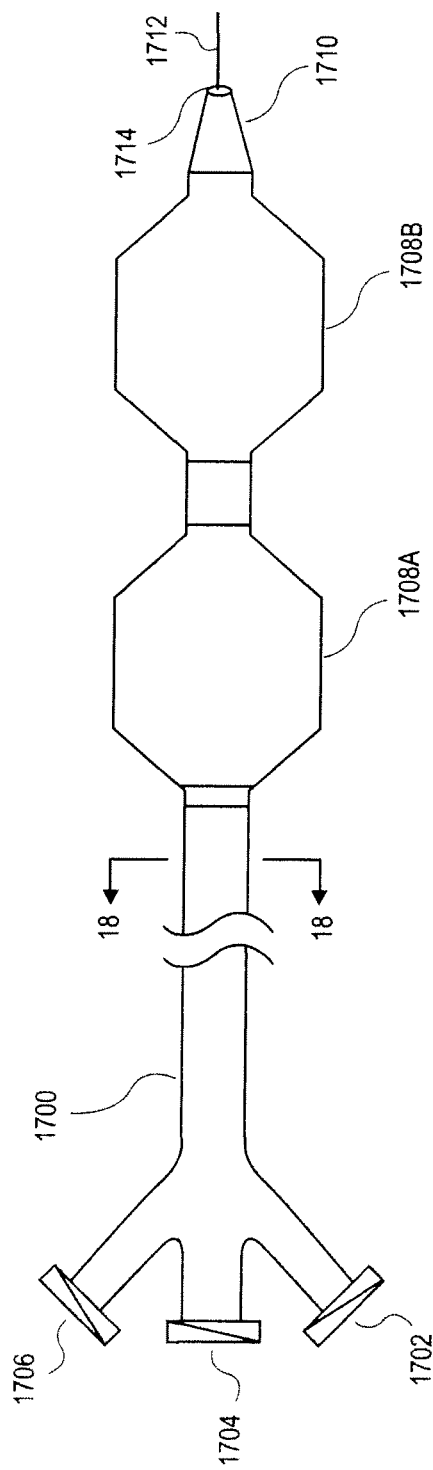
FIG. 17 is an elevational view of a fourth reperfusion catheter employing features of the invention.

FIG. 17 is an elevational view of a fourth reperfusion catheter 1700 employing features of the invention. This catheter 1700 includes expandable members for occluding a vessel and for providing a mechanical plunging action that can urge thrombotic material to a more distal location within the vasculature. In addition, catheter 1700 provides a fluid delivery service to be used in conjunction with this catheter in order to increase or decrease the expandable member profile.

Catheter 1700 generally can include shaft 1701, ports 1702, 1704, and 1706, tapered tip 1710, guidewire 1712, guidewire lumen 1714, and expandable members 1708A-B. In one embodiment, expandable members 1708A-B include a proximal expandable member 1708A and a distal expandable member 1708B. Port 1702 is a proximal balloon inflation port, port 1704 is a guidewire port, and port 1706 is a distal balloon inflation port. In one embodiment, catheter 1700 is capable of being delivered over a guidewire through the patient's anatomy. In one embodiment, expandable members 1708A-B are balloon components. In another embodiment, other types of expandable members known in the art may be employed. In this embodiment, each of the balloon components are placed in fluid communication with a proximal hub (not shown) through a fluid lumen that allows the fluid or gas to be delivered into, or aspirated from the balloon working volume. Thus, the balloons can be, independently or in concert, inflated and deflated by delivering inflation fluid through the independent lumens. For example, and in one embodiment, proximal expandable member 1708A is in fluid communication with proximal balloon inflation port 1702, which is used to inflate and deflate the proximal expandable member 1708A. As another example and in another embodiment, distal expandable member 1708A is in fluid communication with distal balloon inflation port 1702, which is used to inflate and deflate the distal expandable member 1708A. In one embodiment, catheter 1700 includes radio-opaque markers that are used to locate one or more of the different components of catheter 1700. For example and in one embodiment, the one or more radio-opaque markers are markers known in the art and are used to locate the proximal expandable 1708A and a distal expandable 1708B members of the catheter 1700. Guidewire 1712 is a guidewire enters though guidewire port 1704, through the tapered tip 1710, and out distally the guidewire lumen 1802. In one embodiment, guidewire lumen 1802 can be used for a guidewire or delivery of therapeutic agents.

In another embodiment, the guidewire port 1704 is not at the proximal end of the catheter 1700, but along the shaft of catheter 1700. For example and in one embodiment, the guidewire is introduced through a port that is proximal to the expandable members 1708A-B.

Figure 18:
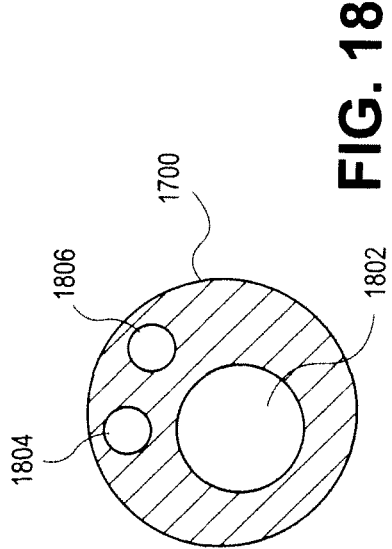
FIG. 18 is a transverse cross sectional view of the catheter of FIG. 17, taken along lines 18-18.

FIG. 18 is a transverse cross sectional view of the catheter 1700 of FIG. 17, taken along lines 18-18. In FIG. 18, catheter 1700 can include three lumens: a guidewire lumen 1802; a lumen 1804 for proximal inflation; and a lumen 1806 for distal inflation. In this FIGURE, the lumens 1802, 1804, and 1806 are shown in an asymmetrical orientation. It will be appreciated that the lumens may be positioned, sized, and configured in accordance with this invention such that they are capable of being used for their intended purposes as described herein. It will also be appreciated that catheter 1800 may not be a solid polymer throughout the cross section as shown, but may in fact comprise several independent tubes maintained within the inner member in the desired location.

The catheter 1700 may be fabricated using materials and processes that are well known in the art of medical device catheters. For example, and in one embodiment, the catheter 1700 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density. In addition, expendable members 1708A-B may be formed from suitable materials, such as polyvinylchloride, polyethylene terephthalate, nylon, Pebax™, silicone, thermoplastic elastomer, and/or other suitable materials known in the art. The expandable members 1708A-B may be compliant, semi-compliant, or non-compliant. For example and in another embodiment, the proximal expandable member 1708A may be formed from a compliant material and the distal expandable member 1708B may be formed from a less than compliant material. In this embodiment, the proximal expandable member 1708A can seal against the vessel regardless of the diameter and the distal expandable member 1708B can be rigid enough to plunge the blood more effectively, as explained below with reference to FIGS. 19A-D.

In one embodiment, either of expandable members 1708A-B are able to occlude the lumen of an artery or other vessel (e.g., circular, eccentric, irregular, etc.) and block flow through this artery. In one embodiment, a compliant expandable member (e.g., 1708A, 1708B, or both 1708 A-B) is made of compliant material that will conform to the shape of the artery and minimizing stretching or trauma to the artery.

FIGS. 19A-D illustrate treating a vessel narrowing caused by an ischemic event. In FIG. 19A, the vessel 1900 has a narrowing caused by an ischemic event. As illustrated, lesion 1902 constricts the flow of blood through vessel 1900. For example and in one embodiment, there is minimal or no blood flow through the narrowed channel, placing the tissue at risk in the distal region of the heart.

Catheter 1700, as illustrated in FIGS. 17-18, can be used in a method to treat a vessel narrowing caused by an ischemic event and providing therapy for the compromised distal region. As illustrated in FIG. 19B, a guidewire 1904 is delivered through the lesion 1902. A subsequent treatment device, such as a stent delivery system or a balloon angioplasty is delivered over the guidewire through the lesions. In one embodiment, a compliant distal member 1708B is used as the stent delivery system. In FIG. 19C, the stent delivery system (e.g., compliant distal member 1708B) is deployed to open the lesion and allow for increased blood flow to the distal tissue. For example and in one embodiment, expandable distal member 1908 deploys to open lesion 1906 in vessel 1900. In one embodiment, there will be some amount of thrombus 1910 that is exposed through the stent struts, as illustrated in FIG. 19D. In FIG. 19D, the lesion 1906 in vessel is opened, although there are thrombi 1910 that are protruding in vessel 1900. This can lead to two detriments: (1) resulting in obstruction of the blood flow; and (2) creating a risk that the thrombus can detach into the bloodstream post-operatively, which may result in a downstream occlusion and subsequent ischemic event. The generated thrombus may enter the bloodstream after stent deployment and could move downstream toward narrower vessels. This can particularly happen when the thrombus is left in the artery at a location proximal to a vessel bifurcation, which can increase the risk of occlusion and an ischemic event.

Figure 20:
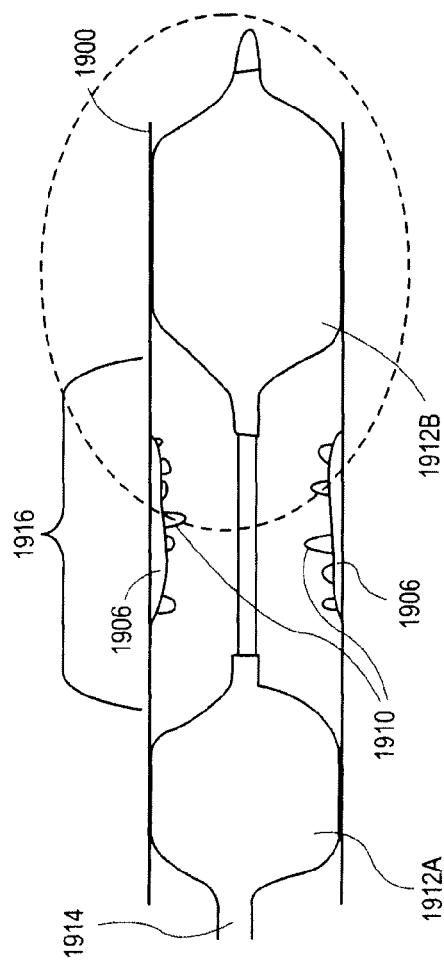
FIG. 20 illustrates the distal balloon of the fourth reperfusion catheter.

In order to disrupt the thrombus that are either not tenaciously attached to the vessel wall, or are suspended, a device in accordance with this invention is tracked into this treatment area. FIG. 20 illustrates a catheter 1914 that can be used to disrupt the thrombus 1910, where the catheter 1914 includes proximal 1912A and distal 1912B expandable members. In one embodiment, catheter 1914 is the catheter 1700 of FIG. 17 above. The proximal 1912A and distal 1912B expandable members may be inflated to larger diameter, either simultaneously or separately. In another embodiment, the catheter balloons 1912A-B are positioned such that one balloon is proximal to the deployed stent or treatment area 1916 (e.g., proximal expandable member 1912A) and the other balloon is positioned distal thereto (e.g., distal expandable member 1912B). For example, in one embodiment, catheter 1914 is positioned such that proximal expandable member 1912A is proximal and the distal expandable member 1912A is distal to the opened lesion 1906 or treatment area 1916.

By positioning catheter 1914 to straddle the treatment area 1916, catheter 1914 can be used to plunge the blood to force thrombus 1910 away from the treatment area 1916.

Figure 21:
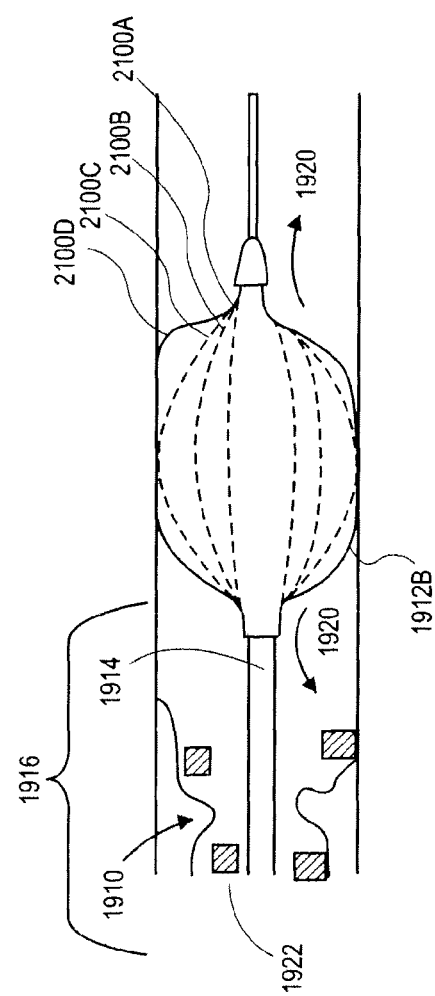
FIG. 21 illustrates various inflation positions of the distal balloon of the fourth reperfusion catheter.

FIG. 21 illustrates various inflation positions of the distal expandable member 1912B of the catheter 1914. In one embodiment, distal expandable member 1912B can be inflated to the various diametric positions 2100A-D that this expandable member passes through as it expands. In one embodiment, the propensity of the central portion of the balloon may be a result of a special balloon design that has a thinner wall thickness toward the center than toward the ends. In this embodiment, inflation fluids introduced into the expandable member 1912B cause the expandable member 1912B to expand near the middle first, and the approximate expansion characteristics are illustrated in positions 2100A-D. Expandable members that preferentially inflate to a maximum diameter near the center region before the lateral balloon regions fully inflate may be contemplated in various ways by one of skill in the art. In one embodiment expandable member 1912A has a similarly structured balloon.

In one embodiment, as expandable member 1912B tends to contact the vessel wall near its middle first, and then the expandable member 1912B shoulders expand in both axial directions, a pressure wave is generated within the blood that propagates in both axial directions. The pressure wave plunges blood in both directions. In this embodiment, the pressure wave causes a pressure wave 1920A that disrupts the loose thrombus 1910 within treatment area 1916 of the vessel 1900 near the stent, and a pressure wave 1920B that affects thrombus 1910 suspended in the vessel distal to the expandable member 1912B. Disrupted thrombus 1910 tends to be forced in the direction of the pressure waves. Therefore, thrombus 1910 shown in the treatment area 1916 will be forced in a proximal direction and the suspended thrombus 1910 distal to the distal expandable member 1912B will be forced in a distal direction. In one embodiment, it will be appreciated that the thrombus 1910 in the treatment area 1916 will be prevented from moving beyond the proximal expandable member 1912A since the proximal expandable member 1912A is inflated during the plunging operation. Thus, the inflation of the proximal expandable member 1912A will create an additional pressure wave that will produce an even greater disruption of the thrombus 1910.

In another embodiment, to further amplify the thrombus 1910 disruption, the proximal and distal expandable members 1912A-B may be cyclically inflated and deflated. The expandable members 1912A-B can be cyclically inflated and deflated simultaneously, alternatively, and/or out-of-phase. This embodiment creates a pulsatile pressure wave within the vessel and effectively plunges the thrombus 1910. The thrombus 1910 will be forced into detaching from the stent or vessel wall 1918 (as illustrated in FIG. 21) and will become suspended within the vessel (e.g., thrombus 1922). In one embodiment, the stent is a device separate from catheter 1914. The loosely attached 1910 and suspended thrombus 1922 distal to the expandable member 1912B will be forced distally. The distally moving thrombus 1910 may still occlude a vessel either partially or fully. However, due to the plunging action of the catheter 1914, thrombus 1910 that lodge within a distal vessel, it is likely that the distal vessel is a smaller vessel that supplies a relatively smaller area of cardiac tissue. Occluding a smaller vessel minimizes possible negative effects of such an occlusion.

In another embodiment, the expandable members 1912A-B of catheter 1914 may be inflated and deflated relative to each other in a number of different sequences. For example and in one embodiment, both the proximal and distal expandable members 1912A-B may be inflated and deflated simultaneously. Alternatively, one of the expandable members 1912A, B may be cyclically inflated and deflated while the other expandable member 1912B, A remains deployed to a larger profile. In this embodiment, the expandable member with the larger profile can be partially or fully deployed. In this alternative embodiment, the proximal expandable member 1912A remains at a larger profile, while the distal expandable member 1912B is cyclically inflated and deflated. The distal expandable member 1912B then produces a pressure wave that displaces thrombus 1910 in the distal direction and allowing for thrombus to flow distally from within the region between expandable members 1912A-B while the distal expandable member 1912B is deflated. In yet another embodiment, the proximal expandable member 1912A is inflated to partially occlude the vessel, thereby providing an effective block to the proximally directed pressure waves. In addition, this embodiment allows for blood to carry thrombus past the distal expandable member 1912B.

Figure 22:
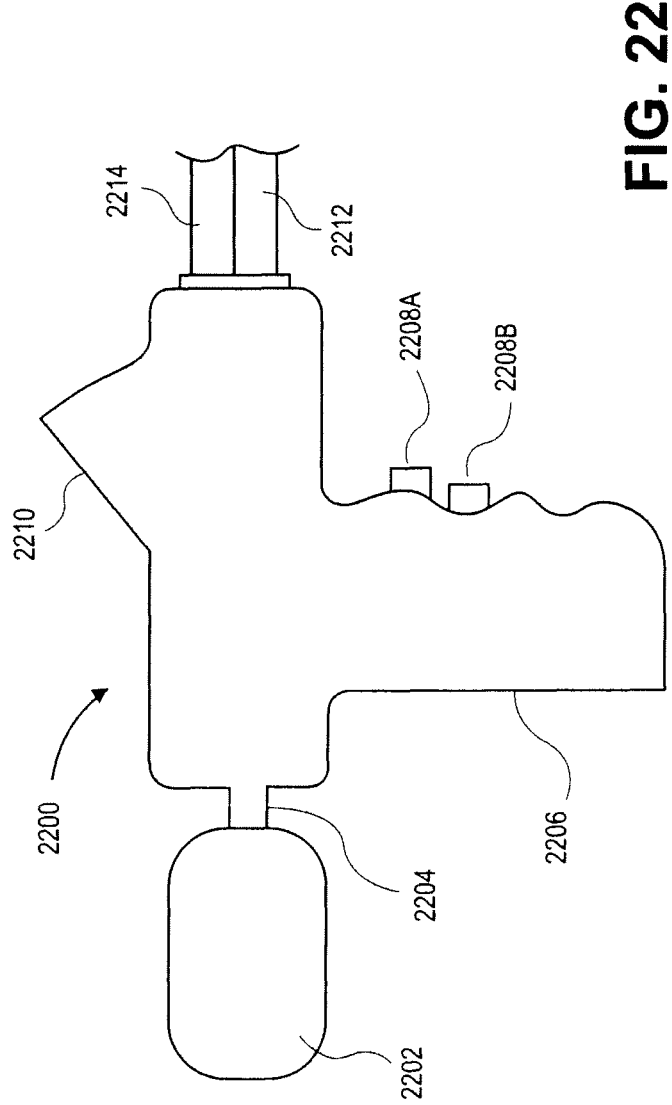
FIG. 22 is an elevational view of inflation/deflation device for the fourth reperfusion catheter employing features of the invention.

In addition, catheter 1914 can be used in combination with an inflation device that allows an operator to easily achieve the different inflation and deflation profiles of the expandable members 1912A-B described above. FIG. 22 is an elevational view of inflation/deflation device 2200 for the fourth reperfusion catheter employing features of the invention. Inflation/deflation device 2200 can include fluid source 2202, syringe/fluid reservoir connector 2204, handle 2206, fluid valve actuation buttons 2208A-B, display 2210, distal inflation lumen 2212, and proximal inflation lumen 2214.

In one embodiment, fluid source 2202 includes a chamber capable of holding an appropriate fluid that can be used to inflate the expandable members of the fourth reperfusion catheter (e.g., one or both of expandable members 1908A-B of catheter 1914 as described in FIGS. 19A-D and 20-21 above). The appropriate fluid in this embodiment can be can be saline, contrast fluid, etc., as known in the art. The fluid contained in fluid source 2202 may be directed to distal 2212 and proximal 2214 inflation lumens via syringe/fluid reservoir connector 2204. In one embodiment syringe/fluid reservoir connector 2204 couples fluid source 2202 with handle 2206 and distal 2212 and proximal 2214 inflation lumens. In another embodiment, fluid is directed from fluid source 2202 through fluid channels and/or other lumens incorporated into the body of inflation/deflation device 2200. In this embodiment, these fluid channels and/or other channels can couple with distal 2212 and proximal 2214 inflation lumens.

In one embodiment, distal 2212 and proximal 2214 inflation lumens are capable of coupling to the distal and proximal ports of the fourth reperfusion catheter (e.g., ports 1706 and 1702 of catheter 1700 as described in FIG. 17 above). In this embodiment, lumens 2212 and 2214 serve as the output for the inflation device 2200.

Fluid activation buttons 2208A-B may be used by an operator of inflation/deflation device 2200 to inflate and/or deflate the expandable members of the fourth reperfusion catheter. For example and in one embodiment, fluid activation buttons 2208A-B are used to inflate/deflate the expandable members 1908A-B of catheter 1914. In one embodiment, fluid activation buttons 2208A-B are used to control a set of plungers (not illustrated) that may be incorporated into body of the inflation/deflation device 2200. In this embodiment, the set of plungers can act upon the individual channels to either plunge a fluid into the inflation lumens or remove inflation fluid from the inflation lumens. Moving any of the set of plungers in one direction or another facilitates this action. Linear motors, pressure actuated valves, or any other mechanism known in the art may be used to move one or more of the set of plungers. In another embodiment, inflation/deflation device may more or less fluid activation buttons.

In one embodiment, actuation of the plungers may be initiated by pressing or triggering one or more of the fluid activation buttons 2208A-B to actuate a valve, energize a motor, or otherwise provide a biasing force. A display 2210 may be provided to view or select the rate and/or frequency of the expandable member inflations of the fourth reperfusion catheter. In this embodiment, the inflation/deflation device 2200 operator has control over the parameters of the treatment that employs inflation/deflation device 2200.

In another embodiment where the optimal rate and frequency of the operation is known, a preset profile of parameters may be employed. In this embodiment, a microcontroller or some other logic controller may be used with inflation/deflation device 2200 to control the actuation of the inflation/deflation device 2200 components that are used to control the expandable members of fourth reperfusion catheter according to the selected profile.

Figure 23:
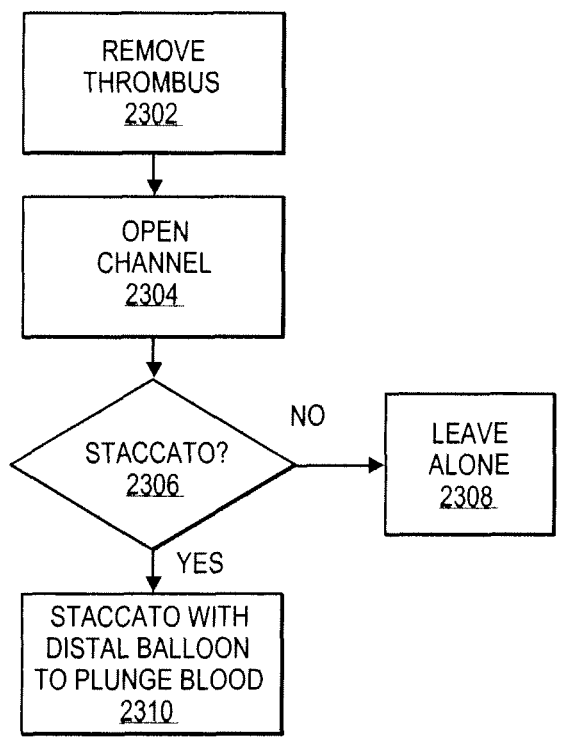
FIG. 23 is one embodiment of a method using the fourth reperfusion catheter to reduce reperfusion injury.

As a result of the cyclical inflation/deflation of the expandable members of the fourth reperfusion catheter, thrombus is disrupted and forced toward distal anatomies and minimizing the risk of tissue damage resulting from vessel occlusion. FIG. 23 is one embodiment of a method 2300 using the fourth reperfusion catheter to minimize the risk of tissue damage resulting from vessel occlusion. Method 2300 is further illustrated with reference to FIGS. 24A-E. FIGS. 24A-E illustrates treating a branched vessel caused by an ischemic event.

Figure 24A:
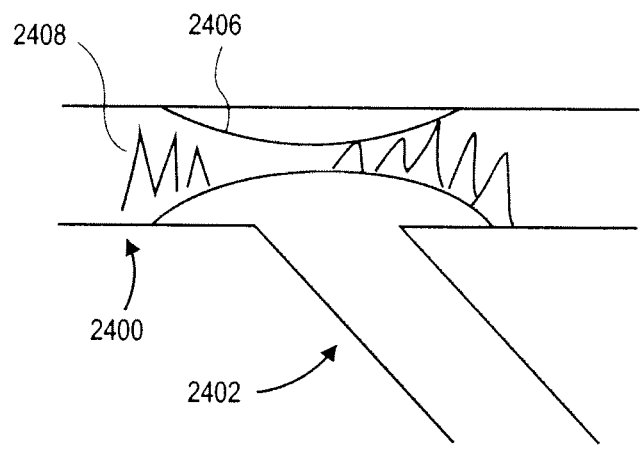
FIGS. 24A-E illustrates treating a branched vessel caused by an ischemic event.
Figure 24B:
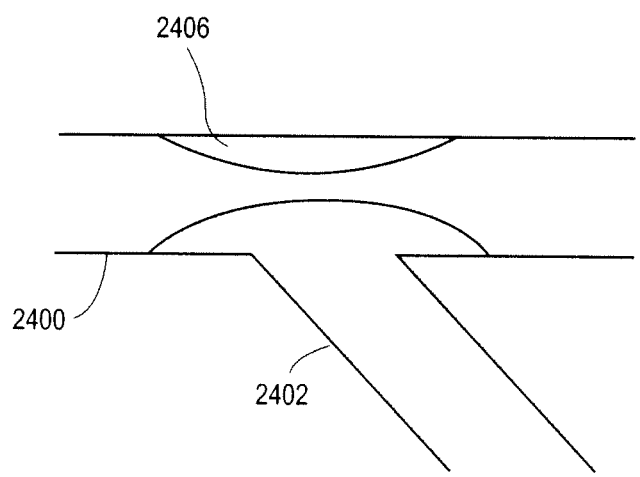

At block 2302, method 2300 removes the thrombus from the occluded vessel. In one embodiment, method 2300 removes the thrombus by aspiration using an aspiration thrombectomy catheter. In one embodiment, vessel 2400 includes an occlusion 2406 and thrombus 2408 that are blocking vessel 2400 as illustrated in FIG. 24A. Vessel 2400 can be partially or completely blocked by occlusion 2406 and/or thrombus 2408. Furthermore, vessel 2400 is coupled to a secondary vessel 2402. As illustrated in FIG. 24A, occlusion 2406 also completely blocks blood access to secondary vessel 2402. In this embodiment, method 2300 removes the thrombus 2408 leaving the occlusion 2406 as illustrated in FIG. 24B. Alternatively, method 2300 can advance the fourth reperfusion catheter over a guidewire through the occlusion.

Figure 24C:

At block 2304, method 2300 opens a channel in the occluded vessel. In one embodiment, method 2300 opens a channel in vessel 2400 by using a stent or some other expandable device to push back the occlusion as known in the art. As illustrated in FIG. 24C, method 2400 pushes back the occlusion such that the former occluding blockage 2410 is pushed back against the walls of vessel 2400. In this embodiment, additional thrombus can be created, for example thrombus 2412, in the secondary vessel 2402.

Figure 24D:
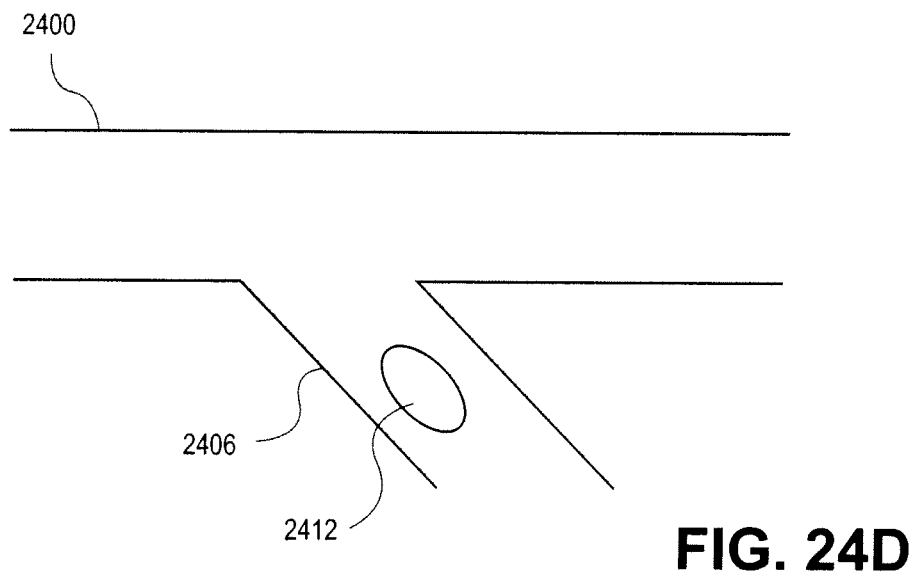
Figure 24E:
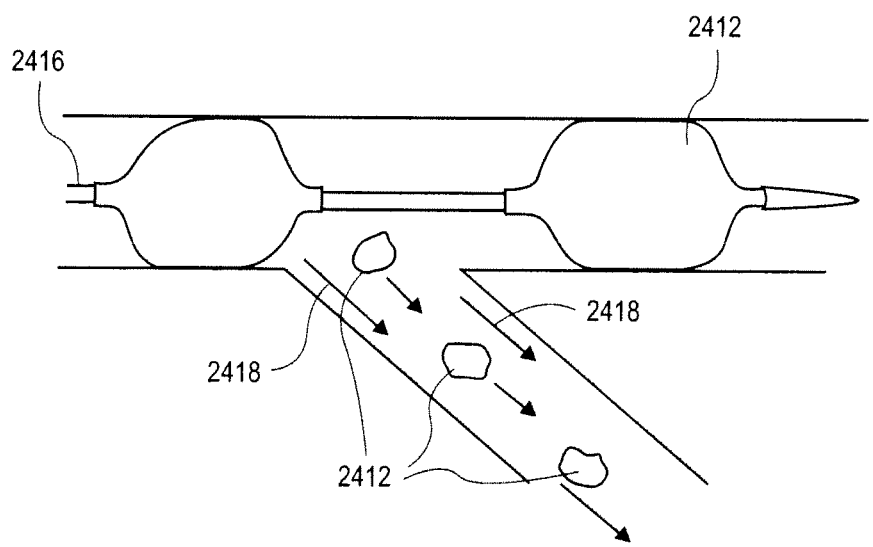

At block 2306, method 2300 determines whether to leave the thrombus alone in the secondary vessel or to staccato the thrombus further down the secondary vessel. If method 2300 determines to leave alone the thrombus, no further action is taken by method 2300 at block 2308. In one embodiment, thrombus 2410 is left alone in the secondary vessel 2402 as illustrated in FIG. 24D.

On the other hand, if method 2300 determines to staccato the thrombus further down the secondary vessel, method 2300 staccatos with a balloon or other appropriate expandable member to plunge the blood at block 2310. In one embodiment, method 2300 plunges the blood with a distal expandable member of catheter 1914 as described in FIGS.

19A-D above. In this embodiment, the distal expandable member creates a pressure wave with the plunging action to carry the thrombus distal from the catheter. For example and as illustrated in the FIG. 24E, the distal balloon 2414 of catheter 2416 creates a pressure wave 2418 that carries the thrombus 2412 distally along the secondary vessel 2402.

The fourth reperfusion catheter further allows for controlled reperfusion of an ischemic artery. The tissue distal to an occlusion is reperfused in coordination with the inflation and deflation of the proximal and distal expandable members. For example, and in one embodiment, when the distal expandable member is deflated, blood advances toward the distal anatomies that were deprived of oxygen. When the expandable member is inflated, blood is prevented from flowing distally. Therefore, the rate at which distal anatomies can be controlled through inflation and deflation of the expandable members of the fourth reperfusion catheter.

In one embodiment, the fourth reperfusion catheter can be used to alternatively inflate and deflate one of the expandable members to induce short periods of ischemia and reperfusion, respectively. In one embodiment, an expandable member is inflated to affect an ischemic event. In one embodiment, the expandable member is inflated for 10-60 seconds and preferably 30 seconds. In alternative embodiment, the expandable member is inflated for shorter or longer periods of time. In addition, the expandable member is deflated and/or left in the deflated position for 10-60 seconds and preferably 30 seconds. In alternative embodiment, the expandable member can be deflated for shorter or longer periods of time. The inflation/deflation is repeated as necessary. For example, and in one embodiment, the expandable member is inflated and deflated as described above 3-10 times.

In an alternative embodiment, the fourth reperfusion catheter can perform reperfusion using alternate methods. For example, and in one embodiment, or more both of the expandable members can be: partially inflated and/or deflate to provide a desired amount of blood flow; and/or inflated and deflated in a manner to provide a specific pattern of flow (e.g., gradual increase or decrease in blood flow) that minimizes reperfusion injury.

In one embodiment, the fourth reperfusion catheter of FIG. 17 can include a valve internal to the expandable members (not illustrated) which allows staged blood flow while the fourth reperfusion catheter is being deployed. Furthermore, in alternative embodiment, the fourth reperfusion catheter of FIG. 17 can include one or more mechanical and/or programmable controllers that would perform the staccato as described above in FIG. 23, block 2310.

Fifth Reperfusion Catheter

Figure 25:
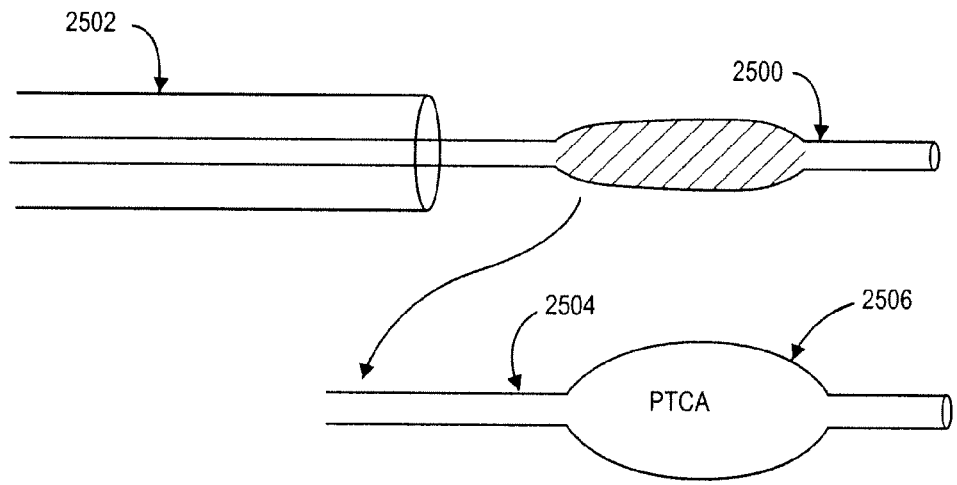
FIG. 25 is an elevational view of a fifth reperfusion catheter employing features of the invention.

FIG. 25 is an elevational view of a fifth reperfusion catheter 2500 employing features of the invention. Catheter 2500 consists of two catheter components that allow catheter 2500 to open an occluded vessel and perform reperfusion without removing catheter 2500 or introducing a subsequent device. In one embodiment, catheter 2500 is capable of being delivered over a guidewire through the patient's anatomy. This catheter 2500 includes an accessory catheter 2502 and inner balloon catheter 2504. The accessory catheter 2502 includes a lumen large enough for the passage of the inner balloon catheter 2504. In one embodiment, accessory catheter 2502 can be of length ranging from long enough for the attachment of the balloon to one that is long enough to exit the body. In another embodiment, for prescription angioplasty balloon/stent delivery applications, accessory catheter 2502 is shorter than the distance from the proximal exit of the guide wire to just proximal to the angioplasty balloon.

Inner balloon catheter 2504 can include a balloon 2506 and a passage lumen (not illustrated). In one embodiment, the balloon 2506 is able to occlude the lumen of an artery or other vessel (e.g., circular, eccentric, irregular, etc.) and block flow through this artery. In one embodiment, the balloon 2506 is made of compliant material that will conform to the shape of the artery and minimizing stretching or trauma to the artery. For example and in one embodiment, inner balloon catheter 2504 is a PTCA catheter as is known in the art.

In one embodiment, the passage lumen is large enough for a gas (e.g., carbon dioxide, etc.) and/or a liquid (e.g., contrast media, etc.) that can be delivered into and removed from the balloon 2506 on the distal end of the catheter 2504. In one embodiment, the passage lumen is long enough to exit the body of a patient. In another embodiment, the passage lumen is attached to a hub to which a standard syringe or indeflator can be attached.

The catheter 2500 may be fabricated using materials and processes that are well known in the art of medical device catheters. For example, and in one embodiment, the catheter 2500 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density. In addition, the balloons of catheter 2500 may be formed from suitable materials, such as polyvinylchloride, polyethylene terephthalate, nylon, and Pebax™.

Figure 26:
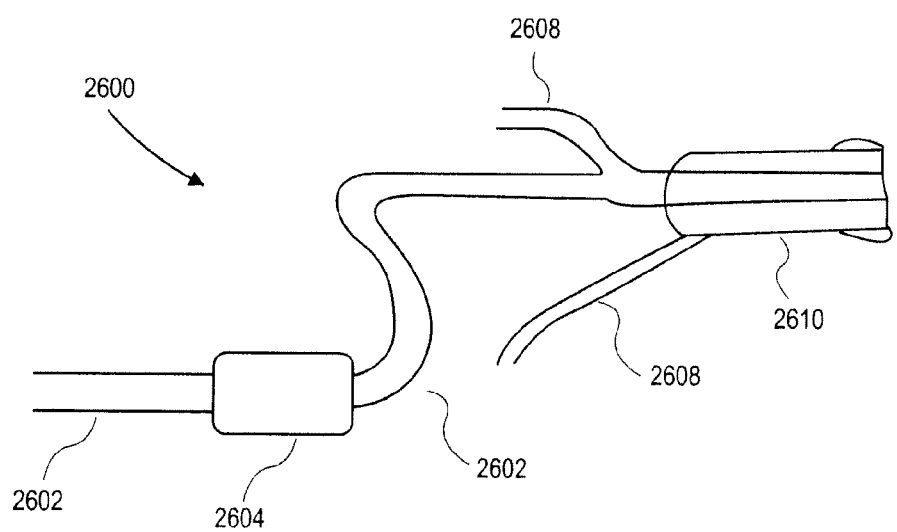
FIG. 26 is an elevational view of a proximal end of the fifth reperfusion catheter.

FIG. 26 is an elevational view of a proximal end of the fifth reperfusion catheter 2600. In FIG. 26, the proximal end of catheter 2600 can include fluid port 2602, hub 2604, fluid connector 2606, guidewire port 2608, and accessory catheter connector 2608. Fluid port 2602 couples with hub 2604 which in turn couples with fluid connector 2606. In one embodiment, fluid port 2602 is capable of introducing a fluid (gas, liquid, etc.) into an accessory balloon (described below). Guidewire port 2608 is port that can be used to introduce a guidewire into catheter 2600. Outer sleeve connector 2608 is a connector that is used to control the outer of catheter 2600.

Figure 27:
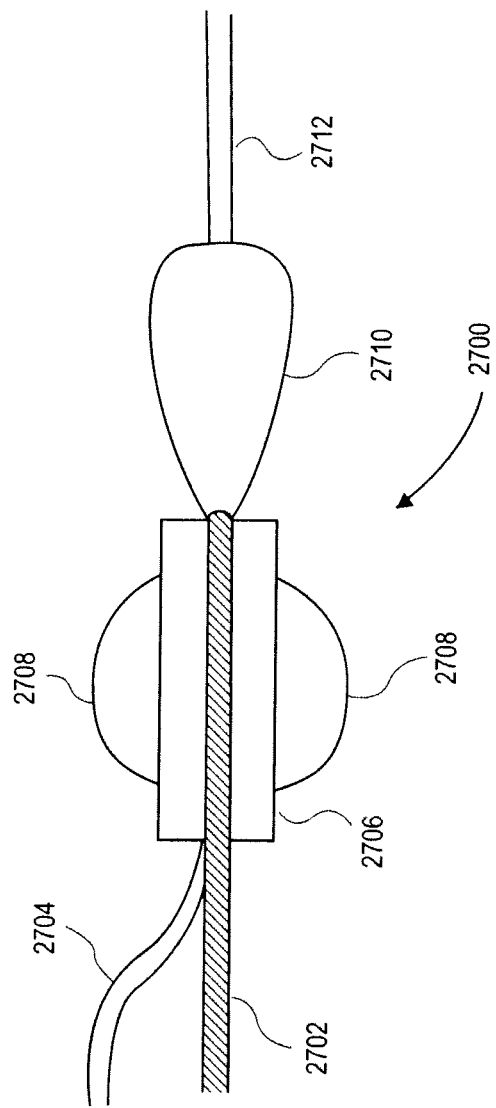
FIG. 27 an elevational view of an accessory balloon occlusion catheter.

FIG. 27 is an elevational view of an accessory balloon occlusion catheter 2700. The accessory balloon occlusion catheter 2700 is a catheter that can be used to perform reperfusion therapy in conjunction with another catheter to open an occluded vessel. In one embodiment, accessory balloon occlusion catheter 2700 includes a lumen so that the accessory balloon occlusion catheter 2700 can slip over the other catheter. In FIG. 27, accessory balloon occlusion catheter 2700 can include inner catheter 2702, outer connector 2704, occlusive sleeve 2706, occlusive balloon 2708, and inner balloon 2710. Inner catheter 2702 is slidably disposed in the accessory balloon occlusion catheter 2700 and can move within occlusive sleeve 2706. In one embodiment, inner catheter 2702 can be a coronary balloon catheter, angioplasty balloon, stent catheter, delivery system, etc. Outer connector 2704 is a used to position the occlusive sleeve 2706 relative to the inner catheter 2702.

Occlusive sleeve 2706 is slidably disposed such that occlusive sleeve can move distally to cover inner balloon 2710 and can move proximally to reveal inner balloon 2710. In one embodiment, occlusive sleeve 2706 can include a locking mechanism that allows the occlusive sleeve 2706 to be locked in a distal position with the occlusive sleeve 2706 covering the inner catheter 2702 and inner balloon 2710.

Alternatively, occlusive sleeve 2706 can be locked in a proximal position revealing the inner catheter 2702 and inner balloon 2710. In one embodiment, occlusive sleeve 2706 includes a hydrophilic coated spring. In another embodiment, the occlusive sleeve can include another locking mechanism as known in the art (e.g., hydrogel, etc.). In one embodiment, inner catheter 2702 includes inner balloon 2710. In one embodiment, inner balloon 2710 is one that can be used to open an occluded vessel.

Figure 28:
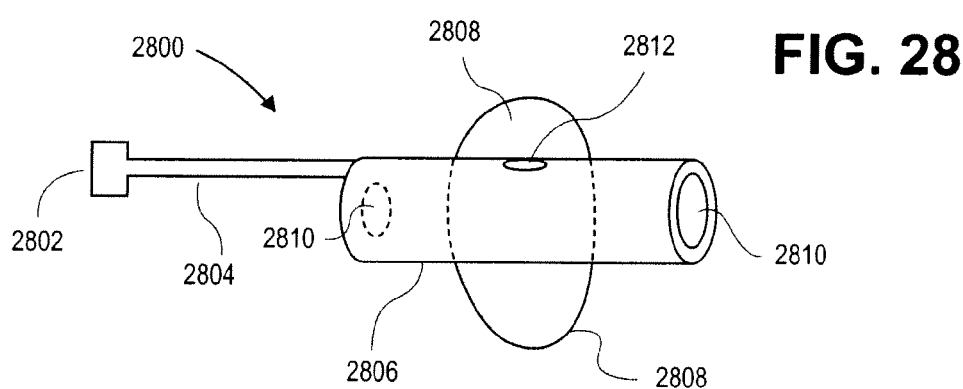
FIG. 28 is an elevational view of an accessory balloon occlusion catheter used for delivering medicine.

In one embodiment, catheter 2700 is used to minimize reperfusion injury. In an alternate embodiment, catheter 2700 can also be used to deliver medicine out the distal end of catheter 2700. FIG. 28 is an elevational view of an accessory balloon occlusion catheter 2800 used for delivering medicine. In one embodiment, accessory balloon occlusion catheter 2800 slides over an angioplasty balloon catheter that may or may include a stent. In FIG. 28, accessory balloon occlusion catheter 2800 includes fluid port 2802, connecting lumen 2804, catheter body 2806, occlusive balloon 2808, catheter lumen 2810, and occlusive balloon fluid port 2812. Fluid port 2802 is in fluid communication with occlusive balloon 2808. Fluid that can be used with catheter 2700 can be air, gas, (e.g., carbon dioxide, etc.), saline, contrast media, etc., or other fluid that can be used to inflate/deflate a balloon. In one embodiment, fluid port 2802 can be used to inflate and/or deflate occlusive balloon 2808 through occlusive balloon fluid port 2812. Connecting lumen 2804 couples fluid port 2802 with the catheter body 2806. In one embodiment, the length of catheter body 2806 is less that a prescription guidewire that is proximal to the angioplasty balloon. In one embodiment, the overall length of catheter 2800 is sufficient to exit the body. Catheter lumen 2810 is a lumen that can be used as a passage for another catheter through catheter 2800. For example and in one embodiment, catheter lumen 2810 can be used as a passage for coronary balloon catheter, angioplasty balloon, stent catheter, delivery system, etc.

Figure 29:
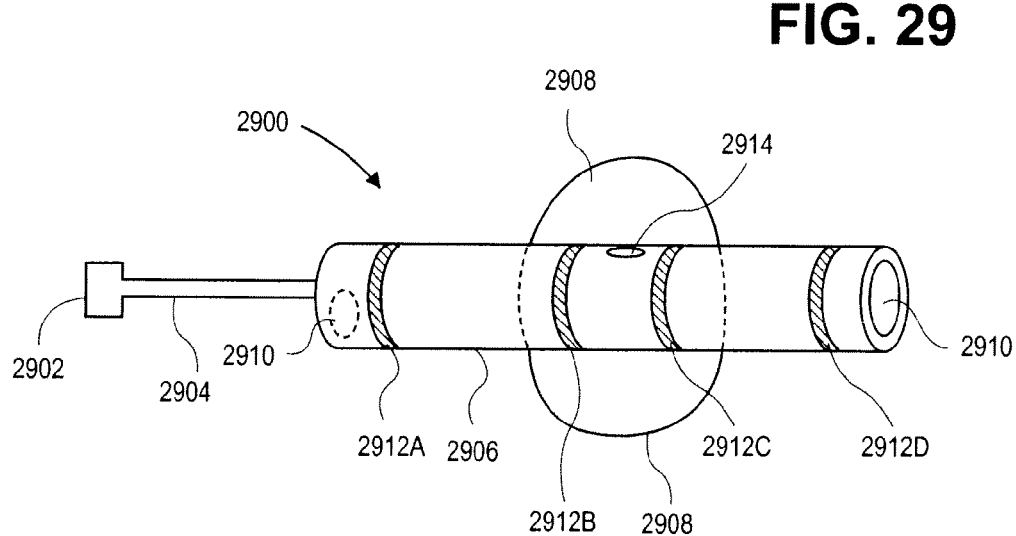
FIG. 29 is an elevational view of an accessory balloon occlusion catheter with radio-opaque markers.

FIG. 29 is an elevational view of an accessory balloon occlusion catheter 2900 with radio-opaque markers. Catheter 2900 can include fluid port 2902, connecting lumen 2904, and catheter body 2906. Catheter body 2906 includes occlusive balloon 2908, catheter lumen 2910, radio-opaque markers 2912A-D, and occlusive balloon port 2914. Fluid port 2902 is in fluid communication with occlusive balloon 2908. Fluid that can be used with catheter 2900 can be air, gas, (e.g., carbon dioxide, etc.), saline, contrast media, etc., or other fluid that can be used to inflate/deflate a balloon. In one embodiment, fluid port 2902 can be used to inflate and/or deflate occlusive balloon 2908 through occlusive balloon fluid port 2914. Connecting lumen 2904 couples the fluid port 2902 with the catheter body 2906.

In one embodiment, the length of catheter body 2906 is sufficient to exit the body. Catheter lumen 2910 is a lumen that can be used as a passage for another catheter through catheter 2900. For example and in one embodiment, catheter lumen 2910 can be used as a passage for coronary balloon catheter, angioplasty balloon, stent catheter, delivery system, etc. In one embodiment, catheter 2900 includes a port (not shown) coupled to catheter lumen 2910 that is used for passage of one of another catheter described above.

In one embodiment, radio-opaque markers 2912A-D are used identify the location of the occlusive balloon 2908 and the proximal and distal ends of catheter body 2906. In one embodiment, there is one radio-opaque marker 2912A located at or near the proximal end of catheter body 2906, two radio-opaque markers 2912B-C located at or near the occlusive balloon 2908, one radio-opaque marker 2912D located at or near the distal end of catheter body 2906. On one embodiment, the radio-opaque markers 2912B-C are located at or near the proximal and distal ends of the occlusive balloon 2908, respectively. Although one radio-opaque marker is illustrated as associated for each end of the catheter body 2906 and two for the occlusive balloon 2908, in alternate embodiments, there are can more or less radio-opaque markers used to locate various components of the catheter body 2906.

Figure 30:
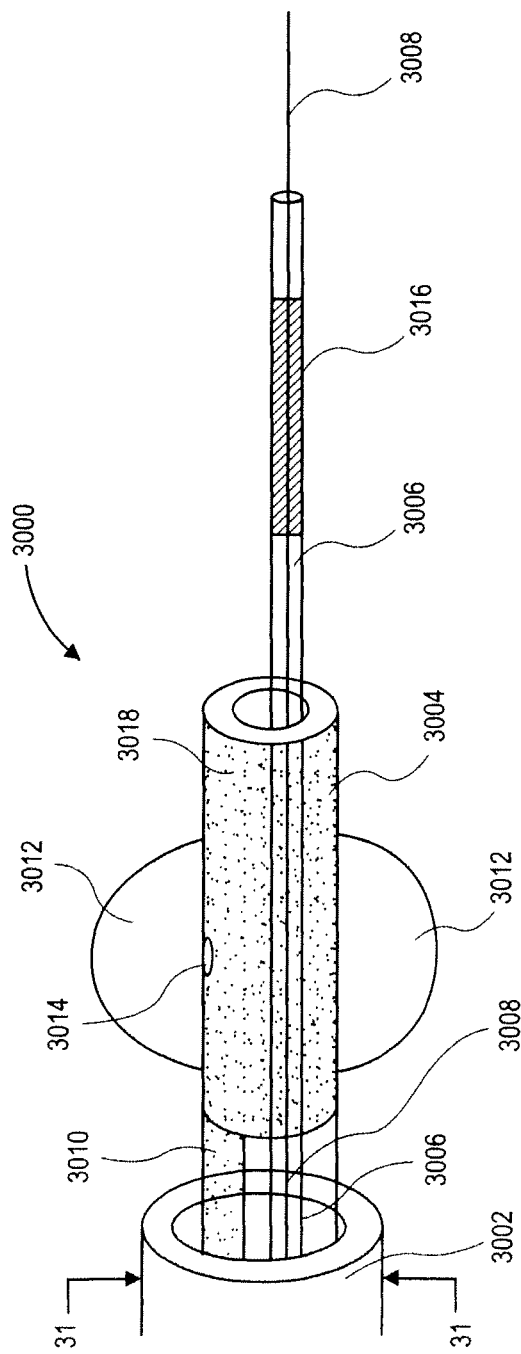
FIG. 30 is an elevation view of an accessory balloon occlusion catheter with a deployed angioplasty balloon catheter.

As described above, the accessory balloon occlusion catheters slide over or within other catheters, such as coronary balloon catheter, angioplasty balloon, stent catheter, delivery system, etc. FIG. 30 is an elevation view of catheter system 3000 that includes guide catheter 3002, an accessory balloon occlusion catheter 3004, and an angioplasty balloon catheter 3006. Accessory balloon occlusion catheter 3004 can be a prescription or a non-prescription as illustrated in FIG. 28 or 29, respectively. In FIG. 30 and in one embodiment, accessory balloon occlusion catheter 3004 is slidably composed within the guide catheter 3002. In one embodiment, guide catheter 3002 can be moved proximally to reveal the occlusive balloon 3012 of accessory balloon occlusion catheter 3004, and can be moved distally to cover up the occlusive balloon 3012. In this embodiment, the accessory balloon occlusion catheter 3004 can be deployed from guide catheter 3002.

In addition, angioplasty balloon catheter 3006 is slidably disposed within accessory balloon occlusion catheter 3004. In one embodiment, accessory balloon occlusion catheter 3004 can be moved proximally to reveal the occlusive balloon 3016 of angioplasty balloon catheter 3006, and can be moved distally to cover up the angioplasty balloon 3016. In this embodiment, the angioplasty catheter 3006 can be deployed from accessory balloon occlusion catheter 3004. In one embodiment, the angioplasty balloon catheter 3006 includes a guidewire 3008

Furthermore, as illustrated, accessory balloon occlusion catheter 3004 can include connector lumen 3010, catheter body 3018, occlusive balloon 3012, and occlusive balloon fluid port 3014.

Figure 31:
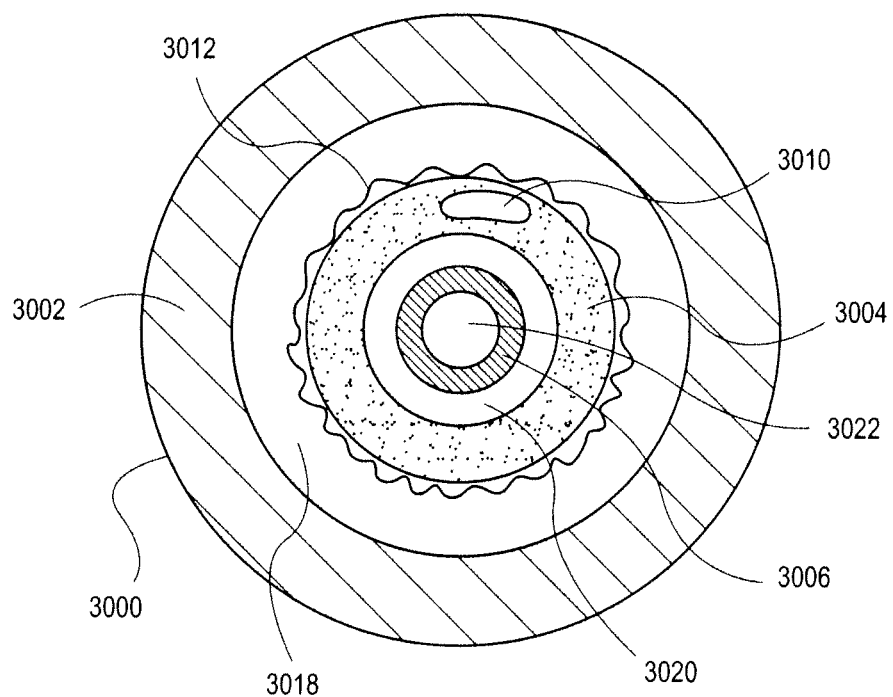
FIG. 31 is a transverse cross sectional view of the catheter of FIG. 30, taken along lines 31-31.

FIG. 31 is a transverse cross sectional view of the catheter system 3000 of FIG. 30, taken along lines 31-31. In FIG. 31, catheter system 3000 includes guide catheter 3002, accessory balloon occlusion catheter 3004, and angioplasty balloon catheter 3006. Angioplasty balloon catheter 3006 includes guidewire lumen 3022 that is used to carry a guidewire. Accessory occlusion balloon catheter 3004 includes catheter lumen 3020 and connector lumen 3010. In addition, angioplasty balloon catheter 3006 is slidably disposed within catheter lumen 3020. As described above, connector lumen 3010 couples the occlusive balloon fluid port 3014 with a port on the proximal end of the catheter 3000 to allow an operator to inflate/deflate the occlusive balloon 3012. Guide catheter 3002 includes catheter body 3018. Accessory occlusion balloon catheter 3004 is slidably disposed within catheter body 3018.

Figure 32:
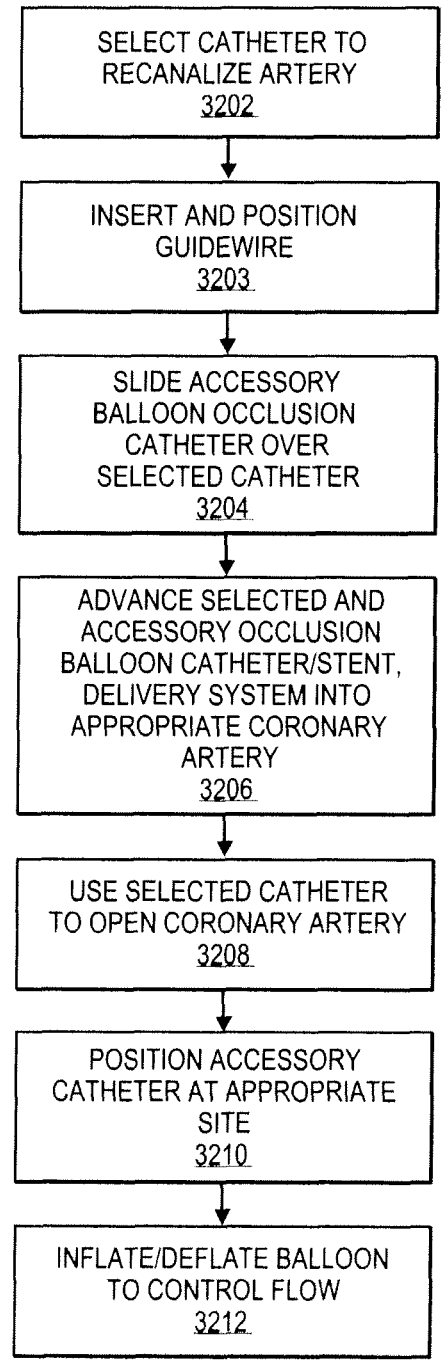
FIG. 32 is one embodiment of a method using the fifth reperfusion catheter to reduce reperfusion injury.

FIG. 32 is one embodiment of a method 3200 using the fifth reperfusion catheter to reduce reperfusion injury. In FIG. 32, method 3200 selects the catheter that will be used to recanalize the vessel at block 3202. In one embodiment, the selected catheter is angioplasty catheter, coronary balloon catheter, stent catheter, delivery system, etc. or another type of catheter known in the art that can be used to open an occlusion in a vessel.

At block 3204, method 3200 assembles a catheter system by sliding the accessory balloon occlusion catheter over the selected catheter. The resulting catheter system allows a catheter operator to open an occlusion in a vessel and perform reperfusion therapy without removing the catheter system from a patient's body. In one embodiment, the resulting catheter system is catheter system as illustrated in FIG. 30 above. Accessory balloon occlusion catheter can be a prescription accessory balloon occlusion catheter (as illustrated in FIG. 28) or a non-prescription accessory balloon occlusion catheter (as illustrated in FIG. 29).

At block 3206, method 3200 advances the catheter system into the appropriate coronary artery. In one embodiment, the catheter system is introduced into a patient's body into the appropriate artery and advanced along that artery as is known in the art.

Method 3200 uses the selected catheter to create an opening in the coronary artery at block 3206. In one embodiment, method 3200 inflates, deflates, and re-positions an angioplasty balloon to create the opening. In another embodiment, method 3200 uses the stent in a stent catheter to stent an opening in the occlusion. In other embodiments, method 3200 uses other method appropriate for the selected catheter to create an opening in the occluded vessel.

At block 3208, method 3200 positions the accessory catheter at an appropriate site to perform the reperfusion therapy. In one embodiment, method 3200 positions that accessory catheter proximal or distal to the opened occlusion or in the middle of the opened occlusion. In another embodiment, method 3200 positions a non-prescription occlusive catheter with the use of the radio-opaque markers on the non-prescription occlusive catheter. In this embodiment, method 3200 uses the radio-opaque marker that are near the proximal and distal ends of the accessory balloon as illustrated in FIG. 29 above.

At block 3212, method 3200 inflates and deflates the accessory balloon to control the blood flow in the occluded vessel. In one embodiment, method 3200 alternatively inflates and deflates the accessory balloon to induce short periods of ischemia and reperfusion, respectively. In one embodiment, method 3200 inflates the accessory balloon to affect an ischemic event. In one embodiment, method 3200 keeps the balloon inflated for 10-60 seconds and preferably 30 seconds. In alternative embodiment, method 3200 can keep the balloon inflated for shorter or longer periods of time. In addition, method 3200 deflates the balloon and/or leaves the balloon in the deflated position for 10-60 seconds and preferably 30 seconds. In alternative embodiment, method 3200 can keep accessory balloon inflated for shorter or longer periods of time. The inflation/deflation is repeated as necessary by method 3200. For example, and in one embodiment, method 3200 inflates and deflates the accessory balloon as described above 3-10 times.

In an alternative embodiment, method 3200 can perform reperfusion using alternate methods. For example, and in one embodiment, method 3200 partially inflates and/or deflates the accessory balloon to provide a desired amount of blood flow; and/or inflates and deflates the accessory balloon in a manner to provide a specific pattern of flow (e.g., gradual increase or decrease in blood flow) that minimizes reperfusion injury.

Figure 33:
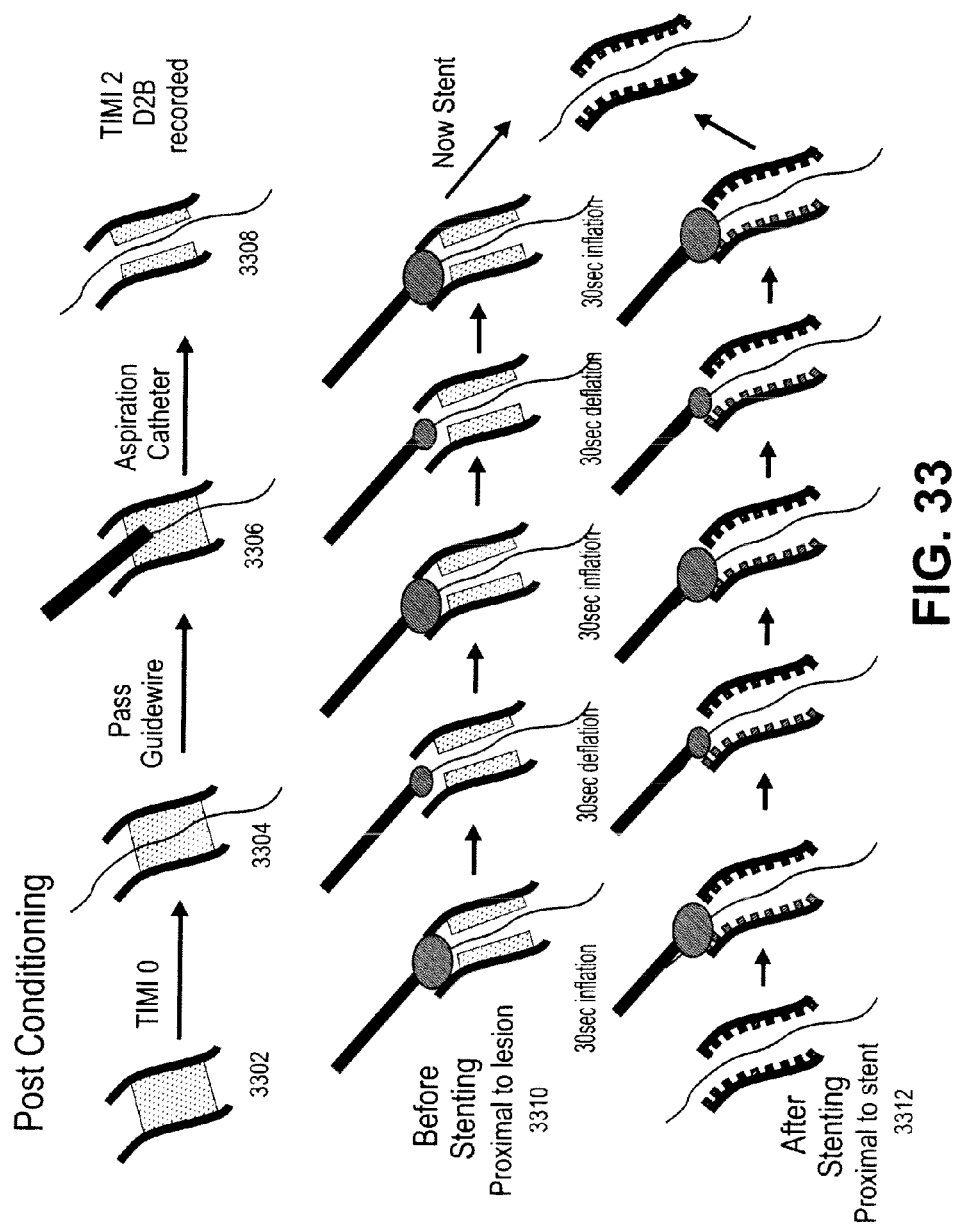
FIG. 33 illustrates treating an occluded vessel with the fifth reperfusion catheter after an ischemic event.

FIG. 33 illustrates treating an occluded vessel with the fifth reperfusion catheter after an ischemic event. In FIG. 33, a guidewire 3304 is advanced through the occluded vessel 3302. In addition, an angioplasty catheter (or aspiration catheter, coronary catheter, etc.) is advanced through the occlusion using the guidewire 3306. This catheter is deployed to create an opening in the occlusion 3308.

In one embodiment, reperfusion therapy can be performed before stenting the occlusion 3310. In this embodiment, the accessory balloon of the fifth reperfusion catheter is inflated and deflated for cycles of 10-60 seconds. These cycles are repeated as necessary to perform the therapy, preferably 3-10 cycles. In one embodiment, the inflation/deflation cycles are performed for 30 seconds each.

In one embodiment, reperfusion therapy can be performed after stenting the occlusion 3312. In this embodiment, the occluded vessel is stented and the reperfusion therapy is performed. For example, and in one embodiment, the accessory balloon of the fifth reperfusion catheter is inflated and deflated for cycles of 10-60 seconds. These cycles are repeated as necessary to perform the therapy, preferably 3-10 cycles. In one embodiment, the inflation/deflation cycles are performed for 30 seconds each.

In one embodiment, the fifth reperfusion catheter of FIGS. 25-31 can include a valve internal to the balloons 2708 and/or 2710 (not illustrated) which allows staged blood flow while the fifth reperfusion catheter is being deployed. Furthermore, in alternative embodiment, the fifth reperfusion catheter of FIGS. 25-31 can include one or more mechanical and/or programmable controllers that would perform the reperfusion therapy as described above in FIG. 32, block 3212.

Sixth Reperfusion Catheter

Figure 34:
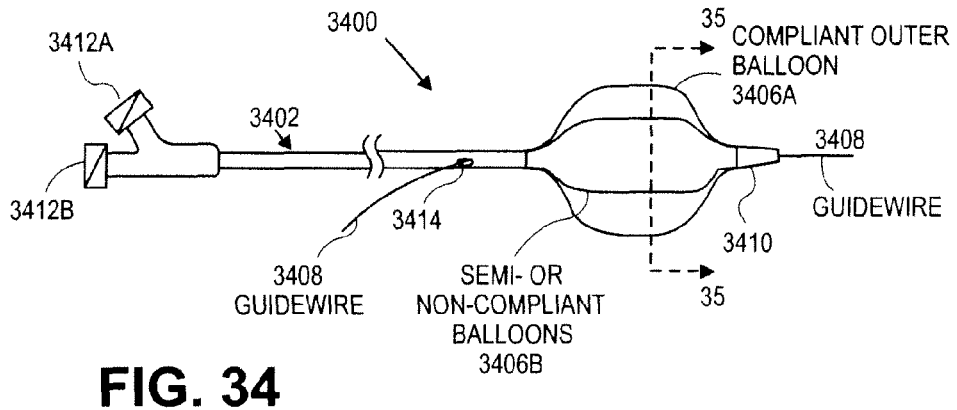
FIG. 34 an elevational view of a sixth reperfusion catheter employing features of the invention.

FIG. 34 an elevational view of a sixth reperfusion catheter 3400 employing features of the invention. In one embodiment, catheter 3400 is capable of being delivered over a guidewire through the patient's anatomy. As with the previously described reperfusion catheters, the catheter 3400 is used to treat blood vessel (arteries, etc.) that have become occluded with thrombus leading to ischemia of tissue distal to the occlusion. For example, an ischemic myocardium that is distal to the occluded coronary artery at a site of thrombus formed secondary is vulnerable to the rupture of a lesion.

Catheter 3400 can generally include ports 3412A-B, shaft 3402, port 3414, balloons 3406A-B, guidewire 3408, and tip 3410. In one embodiment, catheter 3400 includes an outer balloon 3406A that is surrounding an inner balloon 3406B. In this embodiment, the inner balloon 3406B is completely inside the outer balloon 3406A. In one embodiment, the one or more of the ends of the inner balloon 3406B may be in contact with the ends of the outer balloon 3406B. In another embodiment, the inner balloon 3406B ends may not be in contact with the outer balloon 3406A ends. In one embodiment, the outer balloon 3406A is able to occlude the lumen of an artery or other vessel (e.g., circular, eccentric, irregular, etc.) and block flow through this artery.

In one embodiment, balloon port 3412A is in fluid communication with one of outer balloons 3406B, inner balloon 3406A, or both. In another embodiment, balloon port 3412A includes two ports (not illustrated), where each of the balloon ports is in fluid communication with one of the inner 3406B and/or outer 3406A balloons. In another embodiment, port 3412B is in fluid communication with one of outer balloons 3406B, inner balloon 3406A, or both.

In one embodiment, the guidewire 3408 runs the length of the catheter 3400, through tip 3410, and can be used to open an occlusion. This opening can be used subsequently to feed the catheter 3400 into the occlusion. In this embodiment, the guidewire 3408 enters that catheter 3400 at port 3412B. In another embodiment, the guidewire 3408 is introduced further down the catheter at port 3414.

In one embodiment, the balloon structure 3406A-B has a composite structure where the inner balloon 3406B has a lower compliance than the outer balloon 3406A. These balloons can be inflated simultaneously using one or two lumens, or separately with two lumens. For example and in one embodiment, by introducing fluid into a lumen that is in fluid communication with the two balloons, the balloons inflate at substantially the same time. In an alternate embodiment, the balloons can be inflated separately. For example and in one embodiment, one of the inner and outer balloons 3406A-B can be independently inflated using the corresponding balloon port 3412A and lumen 3504. In this embodiment, the volume of fluid used to cycle between occlusion and perfusion of a vessel is minimized. This may improve the procedural time and control over a reperfusion procedure.

In one embodiment, the inner balloon 3406B has a lower compliance than the outer balloon 3406B. For example and in one embodiment, the inner balloon 3406A can be formed from semi- or non-compliant balloon material and the outer balloon 3406B can be formed from a high compliant material. In this example, the inner balloon can be formed from polyvinylchloride, polyethylene terephthalate, nylon, Pebax™, and/or other semi- or non-compliant balloon material known in the art. The outer balloon 3406A can be formed from silicone, thermoplastic elastomer, and/or other compliant balloon material known in the art. In one embodiment, the outer balloon 3406A is made of high-compliant material that will conform to the shape of the artery and minimizing stretching or trauma to the artery. In an alternate embodiment, the outer balloon 3406A is formed from a semi-compliant balloon material and the inner balloon 3406B is formed from a non-compliant material.

The catheter 3400 may be fabricated using materials and processes that are well known in the art of medical device catheters. For example, and in one embodiment, the catheter 3400 may be formed from nylon, urethane, polyurethane, polyvinylchloride, polyester, polyaryletheretherketone, polytetrafluoroethylene, polyvinyldifluoride, Kyner™, polyimide, polyethylene, or any other suitable material of suitable density.

Figure 35A:
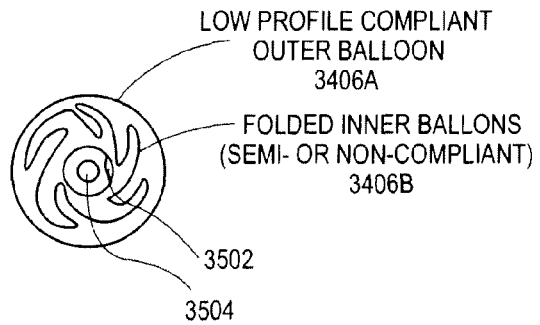
FIG. 35A is a transverse cross sectional view of the catheter of FIG. 34, taken along lines 35-35, where the balloons of catheter are deflated.

FIG. 35A is a transverse cross sectional view of the catheter 3400 of FIG. 34, taken along lines 35-35, where the balloons 3406A-B of catheter are deflated. In FIG. 35A, catheter 3400 can include two lumens: a guidewire lumen 3502 and a balloon lumen 3504. In one embodiment, a guidewire 3408 is capable of sliding through the guidewire lumen 3502. In another embodiment, guidewire lumen 1802 can be used for a guidewire or delivery of therapeutic agents.

In one embodiment, balloon lumen 3504 consists of one lumen to simultaneously inflate/deflate balloons 3406A-B as described above. In an alternative embodiment, lumen 3504 includes two lumens, one for each of balloons 3406A-B. In this embodiment, these lumens are used to simultaneously and/or independently inflate/deflate balloons 3406A-B. For example and in one embodiment, lumen 3504 has two lumens that are used to simultaneously inflate balloons 3406A-B to initially occlude a vessel. In this example, once the vessel is occluded, the inner balloon 3406B may remain inflated and the outer balloon 3406A is inflated/deflated to perform reperfusion. A method of reperfusion using this catheter 3400 is further described in FIG. 38 below.

Furthermore, catheter 3400 includes balloons 3406A-B, which, as illustrated, are deflated. In this embodiment, the inner balloon 3406B is folded inside the deflated outer balloon 3406A. In this embodiment, semi- or non-compliant balloons (e.g., inner balloon 3406B) typically fold when deflated, whereas a compliant balloon (e.g., outer balloon 3406A) will typically relax to a low profile configuration. Thus, when the balloons 3406A-B are deflated, the inner balloon 3406B folds inside the low profile outer balloon 3406A.

Figure 35B:
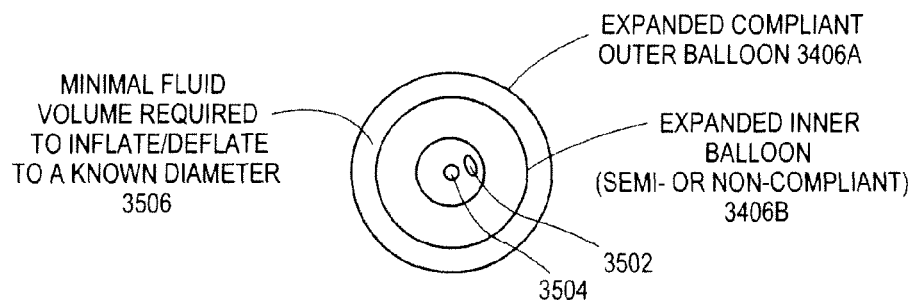
FIG. 35B is a transverse cross sectional view of the catheter of FIG. 34, taken along lines 35-35, where the balloons of catheter are inflated.

FIG. 35B is a transverse cross sectional view of the catheter 3400 of FIG. 34, taken along lines 35-35, where the balloons 3406A-B of catheter 3400 are inflated. In FIG. 35B, catheter 3400 includes the same components as in FIG. 35A above (e.g., guidewire lumen 3502, balloon lumen 3504 consisting of one or two lumens, and balloons 3406A-B). In this embodiment, however, the balloons 3406A-B are inflated. In one embodiment, during inflation, the inner balloon 3406B may reach a maximum diameter according to the stiffness of the balloon material and the material compliance (semi, non, etc.). In this embodiment, the outer balloon 3406B may be able to expand to a larger diameter until the outer balloon 3406A contacts and occludes the vessel that the catheter 3400 is disposed within. With both balloons 3406A-B inflated, there exists a volume between the inner 3406B and outer 3406A balloons that can be filled/emptied with inflation fluid. This volume can be used with minimal fluid 3506 to inflate/deflate the outer balloon 3406A to perform reperfusion.

Figure 36:
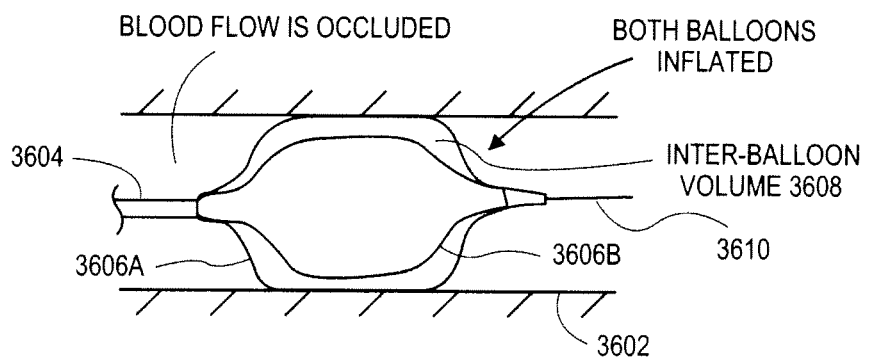
FIG. 36 illustrates the sixth reperfusion catheter inflated in a vessel so as to block fluid flow.

FIG. 36 illustrates the sixth reperfusion catheter 3604 inflated in a vessel so as to block fluid flow. In FIG. 36, the occlusion phase of the catheter 3406 is illustrated. In this phase, both balloons 3606B are inflated so as to occlude the vessel 3602 so as to prevent fluid flow, which can induce an ischemic event. In one embodiment, the balloons 3606A-B can be inflated with air, gas, (e.g., carbon dioxide, etc.), saline, contrast media, etc., or other fluid that can be used to inflate/deflate a balloon. With the balloons inflated, the inflation fluid in the outer balloon occupies an inter-balloon volume 3608. In one embodiment, this inter-balloon volume is smaller than the overall volume of the outer balloon 3606A. In a reperfusion procedure, with the inner balloon 3606B inflated, ischemia and perfusion can be accomplished by inflating/deflating with enough inflation fluid to occupy the inter-balloon volume 3608.

Figure 37:
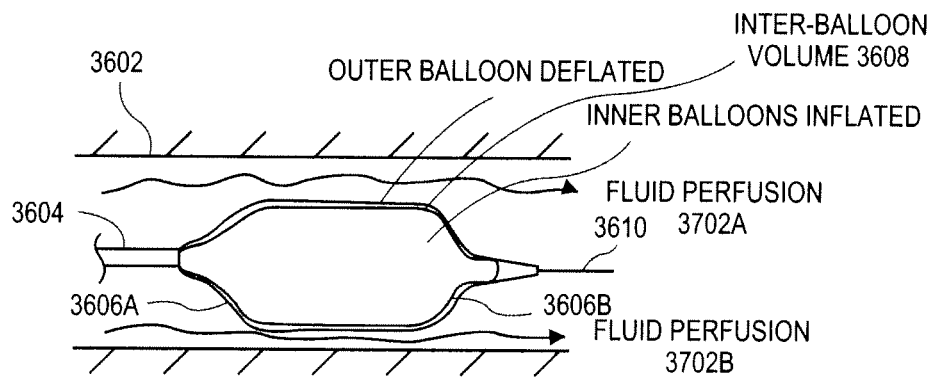
FIG. 37 illustrates the sixth reperfusion catheter with the outer balloon deflated in the vessel so as to allow fluid flow.

FIG. 37 illustrates the sixth reperfusion catheter 3604 with the outer balloon 3606A deflated in the vessel so as to allow fluid flow. In FIG. 37, the outer balloon 3606A is deflated while the inner balloon 3606B remains inflated. In one embodiment, to effect perfusion, the outer balloon 3606A is deflated until the outer balloon 3606A loses contact with the vessel 3602 and contacts the outer surface of the inner balloon 3606B. The outer balloon 3606A deflation opens an area between the balloons 3606A-B and the vessel to allow fluid flow 3702A-B around the balloons 3606A-B. In this embodiment, the deflated outer balloon 3606A allows the vessel distal to the catheter 3606 to be perfused.

In one embodiment, inflation and deflation of the outer balloon can be controlled to produce a reperfusion cycle. In one embodiment, an operator of the catheter can remove the fluid by pulling a vacuum on the fluid in the outer balloon. This is because the inner balloon limits the deflation diameter of the outer balloon. In another embodiment, the outer balloon is deflated for each reperfusion cycle such the cross-sectional area is approximately the same and the blood flow rate is consistent on each perfusion step. In one embodiment, the speed with which the reperfusion is achieved may be variable because the operator need not be concerned with the volume of fluid introduced and retracted from the outer balloon. For example and in one embodiment, the rate of volume flow for inflation/deflation can be the maximum fluid flow that the lumen and/or balloon can handle. Alternatively, the fluid flow can be less than the maximum fluid flow allowable by the catheter components.

Figure 38:
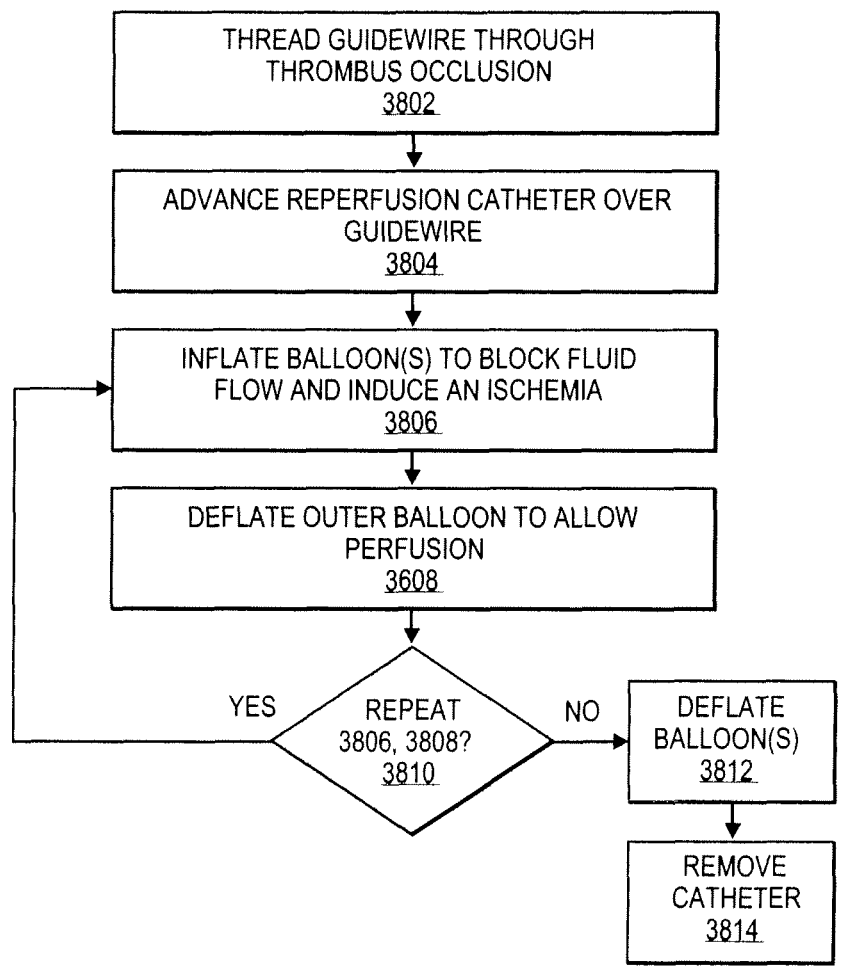
FIG. 38 is one embodiment of a method using the sixth reperfusion catheter to reduce reperfusion injury.

FIG. 38 is one embodiment of a method 3800 using the sixth reperfusion catheter of FIGS. 34-37 to reduce reperfusion injury. In FIG. 38, at block 3802, method 3800 advances the guidewire through the thrombotic occlusion. In one embodiment, guidewire 3408 or 3610 is used to advance through the occlusion with catheter 3400 or 3604, respectively.

At block 3804, method 3800 advances the catheter over the guidewire within the thrombotic occlusion. In one embodiment, method 3800 advances catheter 3400 or 3604 over the guidewire 3408 or 3610, respectively, through the thrombotic occlusion within the opening formed by the guidewire advancement.

Method 3800 inflates the catheter balloons to occlude the vessel, which blocks the fluid flow through the vessel at block 3806. By blocking the flow of the fluid, method 3800 induces short periods of ischemia to the vessel distal to the catheter. In one embodiment, method 3800 inflates the inner and outer balloons 3406A-B simultaneously or independently as described above with reference to FIG. 34 above. For example and in one embodiment, method 3800 initially inflates the inner balloon 3406B and subsequently inflates the outer balloon 3406A to a point where the vessel in occluded. In one embodiment, inflating the inner and outer balloons independently affords greater control over each balloon for the operator of the catheter. Inflation of both balloons may be used to perform a reperfusion step or may be used to initially setup the catheter start a series of reperfusion cycles. In one embodiment, a reperfusion step is a period of ischemia followed by a period of perfusion or visa versa. In one embodiment, method 3800 waits a period of time before proceeding to the next execution block.

Alternatively, if the inner balloon is inflated, method 3800 inflates the outer balloon to occlude the vessel and induce ischemia. This embodiment may be used in a reperfusion step in which the outer balloon is inflated/deflated while the inner balloon remains inflated. In one embodiment, method 3800 waits a period of time before proceeding to the next execution block.

At block 3808, method 3800 deflates the outer balloon to restore fluid and allow a period of perfusion to the vessel distal to the catheter. In one embodiment, method 3800 deflates the outer balloon by removing the fluid in the volume between the inner and outer balloons as described in FIGS. 36-37 above. For example and in one embodiment, method 3800 can remove the fluid by pulling a vacuum on the fluid in the outer balloon. In another embodiment, method 3800 deflates the outer balloon for each reperfusion cycle such the cross-sectional area is approximately the same and the blood flow rate is consistent on each perfusion step.

Method 3800 determines if the reperfusion should be repeated at block 3810. In one embodiment, to perform another reperfusion cycle entails repeating blocks 3806, 3808, and 3810. If method 3800 determines the reperfusion should be repeated, method 3800 proceeds to block 3806 above. If not, method 3800 proceeds to block 3812. At block 3812, method 3800 deflates the balloon(s) that are inflated. For example and in one embodiment, method 3800 deflates the inner balloon be removing the fluid from the inner balloon. This may be done if the outer balloon is inflated or deflated. In another example and another embodiment, method 3800 deflates the outer balloon. The deflation of the balloon(s) may occur simultaneously or independently. At block 3814, method 3800 removes the catheter from the patient.

In one embodiment, method 3800 alternatively inflates and deflates the outer balloon to induce short periods of ischemia and perfusion, respectively. In one embodiment, method 3800 inflates the outer balloon to induce an ischemic event. In one embodiment, method 3800 keeps the outer balloon inflated for 10-60 seconds and preferably 30 seconds. In alternative embodiment, method 3800 can keep the outer balloon inflated for shorter or longer periods of time. In addition, method 3800 deflates the outer balloon and/or leaves the outer balloon in the deflated position for 10-60 seconds and preferably 30 seconds. In alternative embodiment, method 3800 can keep the outer balloon deflated for shorter or longer periods of time. The inflation/deflation is repeated as necessary by method 3800. For example, and in one embodiment, method 3800 inflates and deflates the outer balloon as described above 3-10 times.

In one embodiment, the sixth reperfusion catheter of FIG. 34 can include a valve internal to the balloons 3406A and/or 3406B (not illustrated) which allows staged blood flow while the sixth reperfusion catheter is being deployed. Furthermore, in alternative embodiment, the sixth reperfusion catheter of FIG. 34 can include one or more mechanical and/or programmable controllers that would perform the reperfusion therapy as described above in FIG. 38. In a further embodiment, the outer balloon 3406A can be used to deploy a stent. In one embodiment, the inner balloon can be used to inflate/deflate in a staccato manner. In this embodiment, the sixth reperfusion catheter of FIG. 34 can include one or more mechanical and/or programmable controllers that would perform the staccato.

Alternative Embodiments

The catheters described above are directed to performing reperfusion therapy. In alternative embodiment, these catheters can further be used to deliver therapeutic agents distal to the distal of these catheters. For example and in one embodiment catheters 100, 900, 1200, 1700, 2500, and/or 3400 can include a therapeutic lumen, therapeutic proximal port, and therapeutic distal port. In these embodiments, the therapeutic lumen is used is deliver a therapeutic agent out the therapeutic distal port. These therapeutic agents are introduced into the catheters via the therapeutic proximal port. The therapeutic agents can be delivered before, during and/or after reperfusion therapy.

A variety of suitable agents can be delivered using the catheter(s) and method(s) of the invention, including therapeutic and diagnostic agents. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. A variety of suitable therapeutic agents can be used including but not limited to thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. A variety of diagnostic agents that can be used according to the present invention. According to the present invention, agents described herein may be provided in a variety of suitable formulations and carriers including liposomes, polymerosomes, nanoparticles, microparticles, lipid/polymer micelles, complexes of agents with lipid and/or polymer, and the like.

What is claimed is:

1. A reperfusion catheter, comprising:
an inner member having a proximal shaft portion, a distal shaft portion, and a guidewire lumen, wherein the distal shaft portion includes an inlet hole, a distal port, and a fluid lumen coupling the inlet hole and the distal port, and wherein the inlet hole is in fluid communication with the distal port;

an expandable stent on the distal shaft portion of the inner member and located between the inlet hole and the distal port, wherein the expandable stent includes a side wall;

a cover over the side wall of the expandable stent, wherein the cover includes a proximal end sealed around the inner member distal to the inlet hole; and an outer member that is moveable relative to the inner member, the cover, and the expandable stent between a first position wherein the outer member extends at least partially over the cover and the expandable stent, and a retracted position wherein a distal end of the outer member is disposed proximal to the cover and the expandable stent, the outer member having an inner lumen capable of sliding over the inner member and the cover to capture the expandable stent;

wherein, when the outer member is in the first position within a blood vessel, the distal end of the outer member contacts the cover to block blood flow into the inlet hole, and wherein, when the outer member is in the retracted position within the blood vessel, the inlet hole is disposed between the distal end of the outer member and the cover to allow blood flow into the inlet hole.

2. The reperfusion catheter of claim 1, wherein the guidewire lumen is capable of delivering a therapeutic agent distal to the reperfusion catheter.

3. The reperfusion catheter of claim 1 further comprising a radio-opaque marker on the inner member to locate the expandable stent in a body lumen.

4. The reperfusion catheter of claim 1, wherein the expandable stent includes a self-expanding structure.

5. The reperfusion catheter of claim 4, wherein the cover includes a polymer.

6. The reperfusion catheter of claim 5, wherein the expandable stent includes a tapered shape.

7. The reperfusion catheter of claim 6, wherein the tapered shape includes a gradual transition surface to allow the cover and the expandable stent to be collapsed when the outer member is advanced over the expandable stent.

* * * * *